(12) United States Patent
Wang et al.

(10) Patent No.: US 10,629,822 B2
(45) Date of Patent: Apr. 21, 2020

(54) ORGANIC ELECTROLUMINESCENT MATERIAL AND ORGANIC OPTOELECTRONIC DEVICE

(71) Applicants: Shanghai Tianma AM-OLED Co., Ltd., Shanghai (CN); Tianma Micro-Electronics Co., Ltd., Shenzhen (CN)

(72) Inventors: Xiangcheng Wang, Shanghai (CN); Ying Liu, Shanghai (CN); Hongyang Ren, Shanghai (CN); Wei He, Shanghai (CN); Chen Liu, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 297 days.

(21) Appl. No.: 15/599,244

(22) Filed: May 18, 2017

(65) Prior Publication Data

US 2017/0256723 A1 Sep. 7, 2017

(30) Foreign Application Priority Data

Dec. 30, 2016 (CN) .......................... 2016 1 1259288

(51) Int. Cl.
*H01L 51/00* (2006.01)
*C09K 11/06* (2006.01)
(Continued)

(52) U.S. Cl.
CPC ........ *H01L 51/0072* (2013.01); *C07D 413/04* (2013.01); *C07D 413/10* (2013.01);
(Continued)

(58) Field of Classification Search
CPC .. C07D 413/04; C07D 413/10; C07D 471/04; C09K 11/06; C09K 2211/1007;
(Continued)

(56) References Cited

U.S. PATENT DOCUMENTS

2003/0219625 A1* 11/2003 Wolk ..................... C09K 11/06
428/690
2010/0051106 A1* 3/2010 Kim ..................... C07D 219/14
136/263
2012/0217485 A1* 8/2012 Lee ...................... C07D 403/14
257/40

FOREIGN PATENT DOCUMENTS

CN 105859714 A 8/2016
CN 105936821 A * 9/2016
(Continued)

OTHER PUBLICATIONS

Machine translation for CN 105859714 A (publication date Aug. 2016). (Year: 2016).*
(Continued)

*Primary Examiner* — Dawn L Garrett
(74) *Attorney, Agent, or Firm* — Anova Law Group PLLC

(57) ABSTRACT

A compound and an organic optoelectronic device are provided. The compound has the chemical formula (I): A─[B]$_n$
(Continued)

chemical formula (I). In the chemical formula (I): n denotes a positive integer and 1≤n≤5; a chemical group B has the following chemical formula (II):

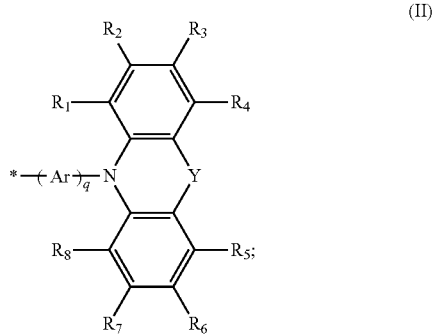

(II)

and a chemical group A has the following chemical formula (III) or (IV):

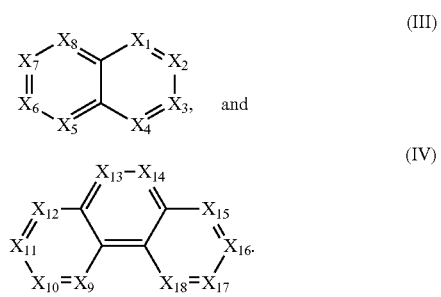

(III)

and (IV)

In the chemical formula (II): $R_1$ to $R_8$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Y is selected from O, S, substituted or unsubstituted imino, substituted or unsubstituted methylene, and substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Ar is selected from $C_6$ to $C_{30}$ aryl, and $C_2$ to $C_{30}$ heteroaryl.

18 Claims, 4 Drawing Sheets

(51) Int. Cl.
*C07D 413/04* (2006.01)
*C07D 413/10* (2006.01)
*C07D 471/04* (2006.01)
*H01L 51/52* (2006.01)
*H01L 51/50* (2006.01)

(52) U.S. Cl.
CPC ............ *C07D 471/04* (2013.01); *C09K 11/06* (2013.01); *H01L 51/0071* (2013.01); *C09K 2211/1007* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(58) Field of Classification Search
CPC ........ C09K 2211/1018; H01L 51/0071; H01L 51/0072; H01L 51/5012; H01L 51/5016; H01L 51/5056; H01L 51/5072; H01L 51/5088; H01L 51/5092; H01L 51/5096; H01L 51/5206; H01L 51/5221
See application file for complete search history.

(56) References Cited

FOREIGN PATENT DOCUMENTS

| | | | |
|---|---|---|---|
| CN | 106047337 A | | 10/2016 |
| KR | 20120117693 A | | 10/2012 |
| KR | 20130142967 A | | 12/2013 |
| KR | 10-2014-0103842 | * | 8/2014 |
| KR | 20140111214 A | | 9/2014 |
| KR | 20160080420 A | | 7/2016 |
| KR | 10-2016-0117823 | * | 10/2016 |
| WO | 2014194971 A1 | | 12/2014 |
| WO | WO 2016/017688 A1 | * | 2/2016 |
| WO | 2016074755 A1 | | 5/2016 |

OTHER PUBLICATIONS

Machine translation for CN 105936821 (publication date Sep. 2016). (Year: 2016).*
Machine translation for WO 2016/017688 (publication date Feb. 2016). (Year: 2016).*
Advanced Optical Materials, (2016), 4(10), pp. 1558-1566. (Year: 2016).*
Machine translation for KR 10-2016-0117823 (publication date Oct. 2016). (Year: 2016).*
Machine translation for KR 10-2014-0103842 (publication date Aug. 2014) (Year: 2014).*
Machine translation for KR 10-2014-0111214 A (publication date Sep. 2014). (Year: 2014).*
Jing Lu, Rational Design of Phenoxazine-based Donor-Acceptor-Donor Thermally Activated Delayed Fluorescent Molecules with High Performance, Physical Chemistry Chemical Physics., 2015, vol. 17, 20014-20020.
Jing Lu et al, Rational Design of Phenoxazine-based Donor-Acceptor-Donor Thermally Activated Delayed Fluorescence Molecules with High Performance, Electronic Supplementary Material (ESI) for Physical Chemistry Chemical Physics, Dec. 31, 2015,18 Pages, vol. No. 17,Royal Society of Chemistry.

* cited by examiner

ORGANIC ELECTROLUMINESCENT MATERIAL AND ORGANIC OPTOELECTRONIC DEVICE

CROSS-REFERENCES TO RELATED APPLICATIONS

This application claims priority of Chinese Patent Application No. 201611259288.X, filed on Dec. 30, 2016, the entire contents of which are hereby incorporated by reference.

FIELD OF THE INVENTION

The present disclosure generally relates to the field of organic electroluminescent material, and, more particularly, relates to an organic electroluminescent material and an organic optoelectronic device thereof.

BACKGROUND

Recently, organic light-emitting diodes (OLEDs) are emerging as a new generation of display products, because of various advantages such as self-luminous, high efficiency, wide color gamut, and wide viewing angle. Organic electroluminescent materials play a critical role for the continuous development of OLEDs.

The organic electroluminescent materials can be excited to generate singlet excited state ($S_1$) excitons and triplet excited state ($T_1$) excitons. According to the spin statistics, the ratio of the $S_1$ excitons to the $T_1$ excitons is 1:3. According to different light-emitting mechanisms, the existing organic electroluminescent materials are often categorized into fluorescent materials, phosphorescent materials, triplet-triplet annihilation (TTA) materials, and heat activated delayed fluorescence (TADF) materials.

TADF materials have the advantages of high quantum yield and low production cost, and comparable luminous efficiency as the phosphorescent material. TADF materials are expected to be new organic electroluminescent materials with great applications. However, the choices of the existing TADF materials are rather limited, and the performance of the TADF materials has not been improved yet. Diverse and high performance TADF materials are highly desired.

The disclosed organic electroluminescent material and organic optoelectronic device thereof are directed to solve one or more problems set forth above and other problems.

BRIEF SUMMARY OF THE DISCLOSURE

One aspect of the present disclosure provides a compound of the following chemical formula (I): A$+$B$]_n$ chemical formula (I). In the chemical formula (I): n denotes a positive integer and $1 \le n \le 5$; a chemical group B has the following chemical formula (II):

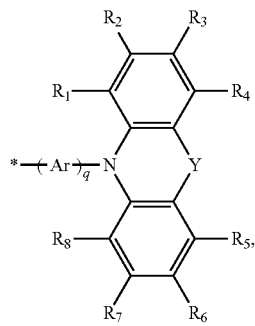

chemical formula (II); and a chemical group A has the following chemical formula (III) or (IV):

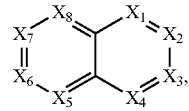

chemical formula (III), an

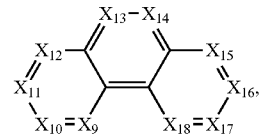

chemical formula (IV). In the chemical formula (II): $R_1$ to $R_8$ are independently selected from hydrogen, deuterium, $C_1$ to $C_{30}$ alkyl, $C_1$ to $C_{20}$ heteroatom-substituted alkyl, $C_6$ to $C_{30}$ aryl, and $C_2$ to $C_{30}$ heteroaryl. Y is selected from O, S, substituted or unsubstituted imino, substituted or unsubstituted methylene, and substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Ar is selected from $C_6$ to $C_{30}$ aryl, and $C_2$ to $C_{30}$ heteroaryl, and q is an integer and $0 \le q \le 3$. In the chemical formula (III): $X_1$ to $X_8$ are independently selected from C and N, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and the chemical group B is connected to C. In the chemical formula (IV): $X_9$ to $X_{18}$ are independently selected from C and N, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and the chemical group B is connected to C.

Another aspect of the present disclosure provides an organic optoelectronic device. The organic optoelectronic device comprises an anode; a cathode; and one or more organic thin film layers disposed between the anode and the cathode. At least one of the one or more organic thin film layers includes one or more organic electroluminescent compounds each having the following chemical formula (I): A$+$B$]_n$ chemical formula (I). In the chemical formula (I): n denotes a positive integer and $1 \le n \le 5$; a chemical group B has the following chemical formula (II):

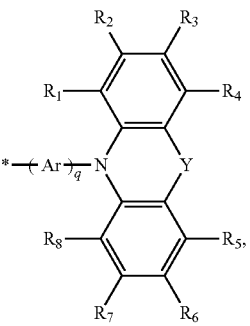

chemical formula (II); and a chemical group A has the following chemical formula (III) or (IV):

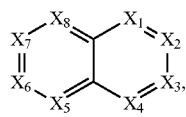

chemical formula (II), and

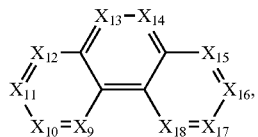

chemical formula (IV). In the chemical formula (II): $R_1$ to $R_8$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Y is selected from O, S, substituted or unsubstituted imino, substituted or unsubstituted methylene, and substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Ar is selected from $C_6$ to $C_{30}$ aryl, and $C_2$ to $C_{30}$ heteroaryl, and q is an integer and $0 \leq q \leq 3$. In the chemical formula (III): $X_1$ to $X_8$ are independently selected from C and N, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}o$ heteroaryl is included, and the chemical group B is connected to C. In the chemical formula (IV): $X_9$ to $X_{18}$ are independently selected from C and N, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and the chemical group B is connected to C.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

In FIGS. 1-5 and 7, the various reference numerals and corresponding names are as follows: 100-substrate; 110-anode; 120-cathode; 130-light-emitting layer; 140-hole transport layer (HTL); 150-electron transport layer (ETL); 160-hole injection layer (HIL); 170-electron injection layer (EIL); 180-electron blocking layer (EBL); and 190-hole blocking layer (HBL).

DETAILED DESCRIPTION

Figure 1:
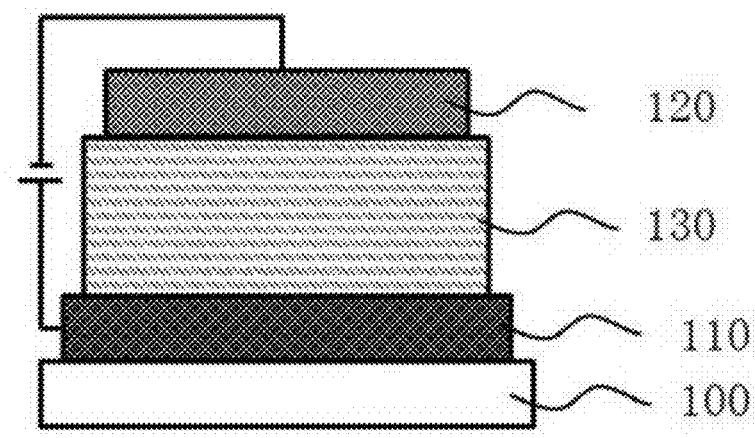
FIG. 1 illustrates a schematic diagram of an exemplary organic light-emitting diode (OLED) consistent with disclosed embodiments.

Reference will now be made in detail to exemplary embodiments of the invention, which are illustrated in the accompanying drawings. Hereinafter, embodiments consistent with the disclosure will be described with reference to drawings. In the drawings, the shape and size may be exaggerated, distorted, or simplified for clarity. Wherever possible, the same reference numbers will be used throughout the drawings to refer to the same or like parts, and a detailed description thereof may be omitted.

Further, in the present disclosure, the disclosed embodiments and the features of the disclosed embodiments may be combined under conditions without conflicts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

As discussed in the background, according to different light-emitting mechanisms, the existing organic electroluminescent materials are often categorized into fluorescent materials, phosphorescent materials, triplet-triplet annihilation (TTA) materials, and heat activated delayed fluorescence (TADF) materials. In fluorescent materials, $S_1$ excitons transit to the ground state $S_0$ by radiation, thereby emitting light. The material cost is substantially low, however, due to the limited number of $S_1$ excitons (i.e., accounting for 25% of the excitons generated by the organic electroluminescent material), the quantum efficiency is substantially low.

Phosphorescent materials not only utilize $S_1$ excitons accounting for 25% of the excitons generated by the organic electroluminescent material, but also utilize $T_1$ excitons accounting for 75% of the excitons generated by the organic electroluminescent material. Thus, the theoretical quantum efficiency of phosphorescent materials is up to 100%, and when used as organic electroluminescent materials for the OLEDs, the phosphorescent materials has significantly improved the luminous efficiency as compared to the fluorescent materials. However, the phosphorescence materials are limited to Ir, Pt, Os, Re, Ru and other heavy metal complexes. The production cost is higher, and the structure is substantially simple.

TTA materials utilize two $T_1$ excitons interactions to produce one $S_1$ exciton that transitions back to the ground state $S_0$ by radiation. Although $T_1$ excitons are utilized, the production cost is not high, and the theoretical maximum quantum yield of TTA materials is only about 62.5%. The practical applications of TTA materials are still rather limited.

TADF materials utilize both $S_1$ excitons accounting for 25% of the excitons generated by the organic electroluminescent material, and $T_1$ excitons accounting for 75% of the excitons generated by the organic electroluminescent material. Thus, the theoretical quantum efficiency of TTA materials is up to 100%. TADF materials are mainly aromatic organic materials without rare metal elements, and the production cost is substantially low.

According to the above discussion of various existing organic electroluminescent materials, TADF materials have high quantum yield, low production cost, and comparable luminous efficiency as the phosphorescent material. TADF materials are expected to be organic electroluminescent materials with great application prospect. However, the choices of the existing TADF materials are rather limited, and the performance the TADF materials has to be improved. Diverse and high performance TADF materials are highly desired.

The present disclosure provides an organic electroluminescent material to be used in an organic optoelectronic device, and an organic optoelectronic device thereof.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are for illustrative only and not intended to limit the scope of the present disclosure.

When no other definition is provided, the term "substituted" used herein means that the hydrogen of the compound is substituted with at least one of the following groups: halogen (F, Cl, Br or I), hydroxy, alkoxy, nitro, cyano, amino, azido, amidino, nitrite, carbonyl, carbamoyl, thiol, ester, carboxyl or salt thereof, sulfonic acid group or salt thereof, phosphoric acid group or salt thereof, $C_1$ to $C_{30}$ alkyl group, $C_2$ to $C_{20}$ alkenyl group, $C_2$ to $C_{20}$ alkynyl group, $C_6$ to $C_{30}$ aryl group, $C_7$ to $C_{20}$ aralkyl group, $C_1$ to $C_8$ alkoxy group, $C_3$ to $C_{20}$ heteroaryl group, and $C_3$ to $C_{30}$ cycloalkyl.

Alkyl group refers to a hydrocarbyl group that is fully saturated (without double or triple bond), which may be linear or branched, or cycloalkyl, and may also be a straight or branched chain containing a cycloalkyl substituent chain. The alkyl group may contain 1 to 30 carbon atoms, 1 to 20 carbon atoms, 1 to 10 carbon atoms or 1 to 6 carbon atoms. The numerical range of "1 to 30" refers to all integers in the range, including 1, 2, 3, 4, 5, 6, 7, 8, 9, 10, 11, 12, 13, 14, 15, 16, 17, 20, 21, 22, 23, 24, 25, 26, 27, 28, 29 or 30. The alkyl group may include, but not limited to, methyl, ethyl, propyl, isopropyl, n-butyl, isobutyl, sec-butyl, tert-butyl, pentyl and hexyl. The alkyl group may be substituted or unsubstituted.

Heteroatom-substituted alkyl group includes an alkyl group substituted at any position by a heteroatom. For example, the heteroatom-substituted alkyl group may be attached to the compound nucleus by a heteroatom, i.e., in a "—Z-alkyl" form, where Z may represent a heteroatom such as O (i.e., oxygen atom), S (i.e., sulfur atom). The heteroatom-substituted alkyl group may also be an alkoxy group. The heteroatom-substituted alkyl group may include 1 to 30 carbon atoms, 1 to 20 carbon atoms, 1 to 10 carbon atoms or 1 to 6 carbon atoms. The numerical range of "1 to 30" refers to all integers in the range, including 1, 2, 3, 4, 5, 6, 7, 8, 9, 10, 11, 12, 13, 14, 15, 16, 17, 20, 21, 22, 23, 24, 25, 26, 27, 28, 29 or 30. The alkoxy group may include, but not limited to, methoxy, ethoxy, propoxy, isopropoxy, and butoxy. The heteroatom-substituted alkyl group may be substituted or unsubstituted.

Aromatic or Aryl group refers to carbocyclic (all carbon) having a completely delocalized π-electron system over all rings, including monocyclic aromatic or polycyclic aromatic groups. The polycyclic aromatic group may include two or more aromatic rings, such as a benzene ring, which are linked to each other by a single bond or by mutual chemical bonds. The number of carbon atoms in the aryl group may vary. For example, the aryl group may contain 6 to 30 carbon atoms. For example, a numerical range of 6 to 30 refers to all integers in the range, including 6, 7, 8, 9, 10, 11, 12, 13, 14, 15, 16, 17, 18, 19, 20, 21, 22, 23, 24, 25, 26, 27, 28, 29 or 30. The aryl group may include, but be not limited to, benzene, biphenyl, naphthalene, anthracene, phenanthrene or pyrene. The aryl group may be substituted or unsubstituted.

Heteroaryl group refers to a monocyclic or polycyclic aromatic ring system comprising one or more heteroatoms in which the heteroatoms are elements other than carbon, including but not limited to nitrogen, oxygen and sulfur. The number of carbon atoms in the heteroaryl ring may vary. For example, the heteroaryl group may include 1 to 20 carbon atoms in the ring, and a numerical range of 1-20 refers to all integers in the range, including 1, 2, 3, 4, 7, 8, 9, 10, 11, 12, 13, 14, 15, 16, 17, 18, 19 or 20. For example, the heteroaryl group may include 1 to 30 ring skeleton atoms in its ring, for example, a numerical range of 1-30 refers to all integers in the range, including 1, 2, 3, 11, 12, 13, 14, 15, 16, 17, 18, 19, 20, 21, 22, 23, 24, 25, 26, 27, 28, 29 or 30.

In addition, the heteroaryl group may include a fused ring system in which two rings, such as at least one aryl ring and at least one heteroaryl ring or at least two heteroaryl rings, share at least one chemical bond. For example, the heteroaryl ring may include, but not limited to, furan, furazan, thiophene, benzothiophene, phthalazine, pyrrole, oxazole, benzoxazole, 1,2,3-oxadiazole, oxadiazole, thiazole, 1,2,3-thiadiazole, 1,2,4-thiadiazole, benzothiazole, imidazole, benzimidazole, indole, indazole, pyrazole, benzopyrazole, Isoxazole, benzisoxazole, isothiazole, triazole, benzotriazole, thiadiazole, tetrazole, pyridine, pyridazine, pyrimidine, pyrazine, purine, pteridine, quinoline, isoquinoline, auinazoline, quinoxaline, cinnoline and triazine. The heteroaryl group may be substituted or unsubstituted.

The present disclosure provides an organic electroluminescent material comprising a compound of the following chemical formula (I):

A—[B]$_n$,  chemical formula (I).

In the chemical formula (I), n denotes a positive integer and 1≤n≤5, and the chemical group B may have the following chemical formula (II):

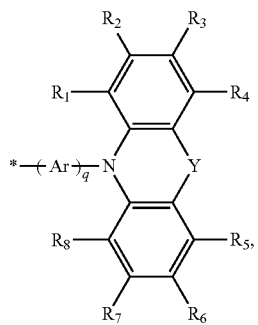

chemical formula (II).

In the chemical formula (II), $R_1$ to $R_8$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Y may be selected from O, S, substituted or unsubstituted imino, substituted or unsubstituted methylene, and substituted or unsubstituted silylene, in which a substituent may be selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Ar may be selected from $C_6$ to $C_{30}$ aryl, and $C_2$ to $C_{30}$ heteroaryl. q is an integer and $0 \leq q \leq 3$.

The chemical group A may have the following chemical formula (III) or (IV):

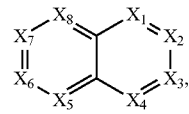

chemical formula (III), and

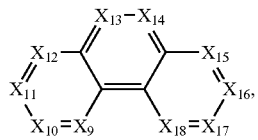

chemical formula (IV).

In the chemical formula (III), $X_1$ to $X_8$ may be independently selected from C and N. When N is selected, a substituent may not be included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl may be included. The chemical group B may be connected to C.

In the chemical formula (IV), $X_9$ to $X_{18}$ may be independently selected from C and N. When N is selected, a substituent may not be included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl may be included. The chemical group B may be connected to C.

In one embodiment, in the chemical formula (III), at least two of $X_1$ to $X_8$ may be selected as N. In another embodiment, in the chemical formula (IV), at least two of $X_9$ to $X_{18}$ may be selected as N.

In certain embodiments, the disclosed compounds may have also the following chemical formula (V):

chemical formula (V)

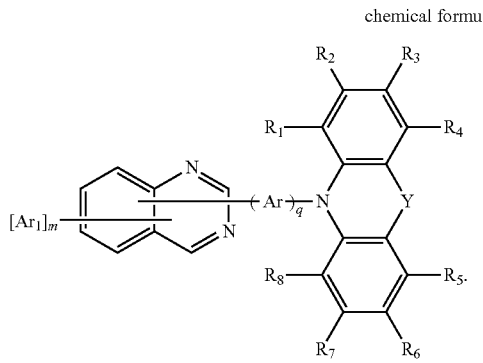

In the chemical formula (V), $Ar_1$ may be selected from $C_6$ to $C_{30}$ aryl, and $C_2$ to $C_{30}$ heteroaryl. m is an integer and $0 \leq m \leq 3$.

In certain other embodiments, the disclosed compounds may have also the following chemical formula (IV):

chemical formula (IV)

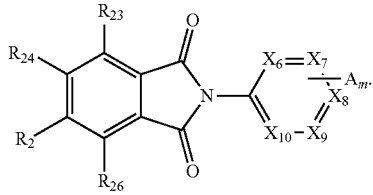

In the disclosed compounds, the chemical formula (IV) may be selected from the following:

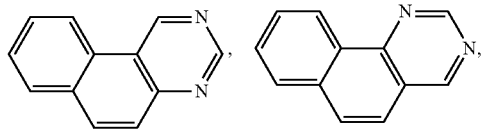

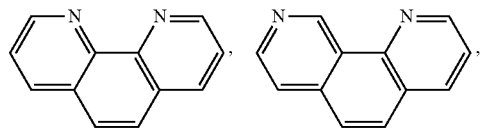

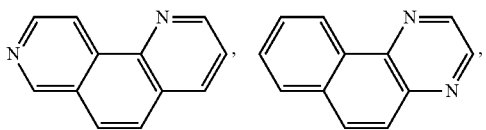

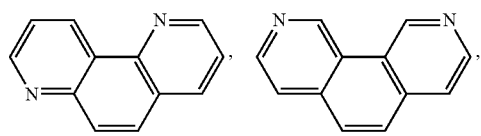

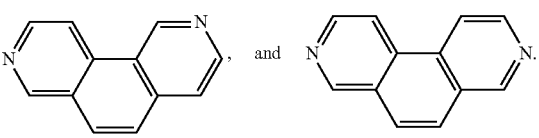

In one embodiment, the $C_6$ to $C_{30}$ aryl may be selected from phenyl and naphthyl.

In one embodiment, $R_1$ to $R_8$ may be selected from hydrogen, and Y may be selected from O, S, dimethyl substituted C(—C(CH$_3$)$_2$—) or dimethyl substituted Si(—Si(CH$_3$)$_2$—).

In one embodiment, n represents an integer of 1 or 2.

In one embodiment, q represents an integer of 0 or 1.

Certain examples of the disclosed compounds are shown below as Compounds 1-198, which are for illustrative purposes and are not intended to limit the scope of the present discourse.

-continued

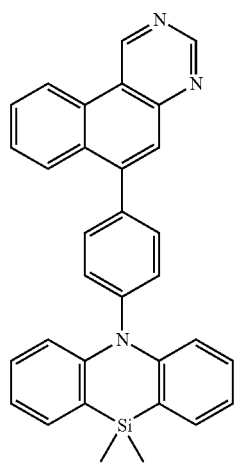
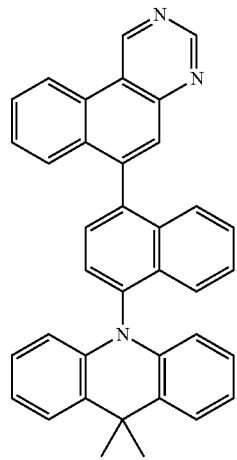

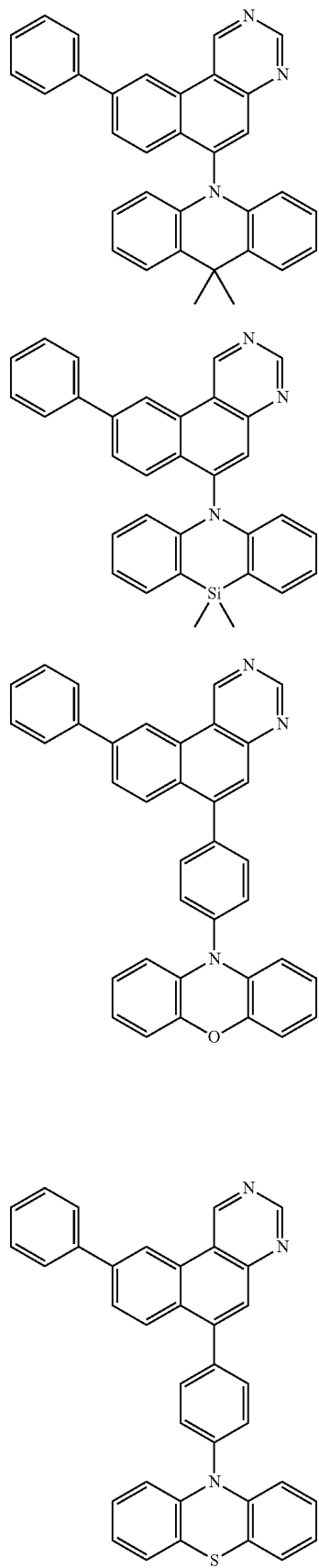
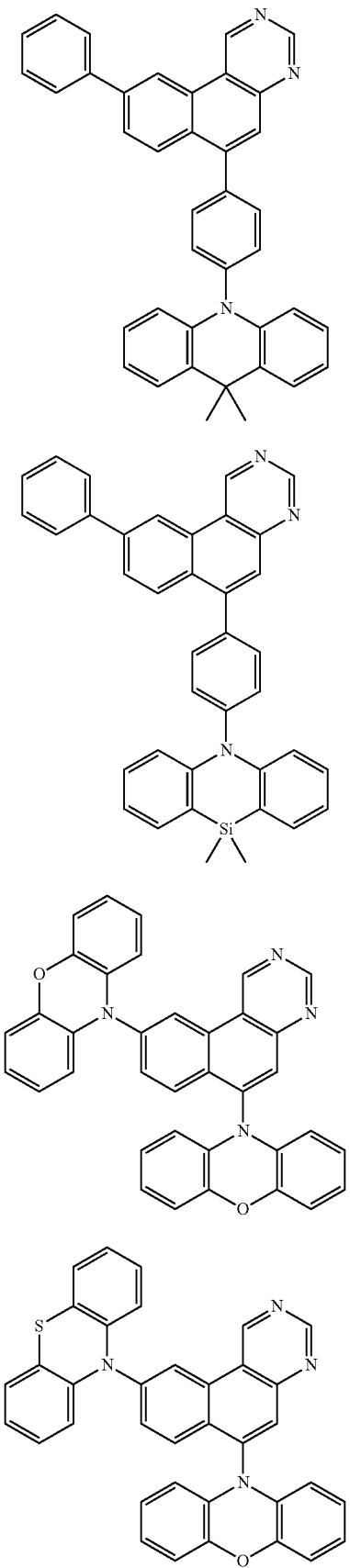

-continued
23
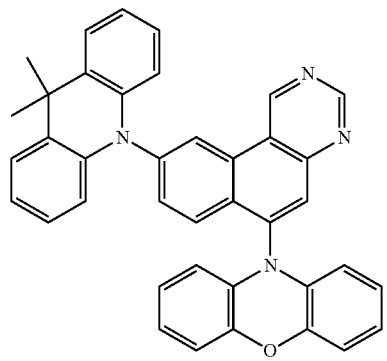
24
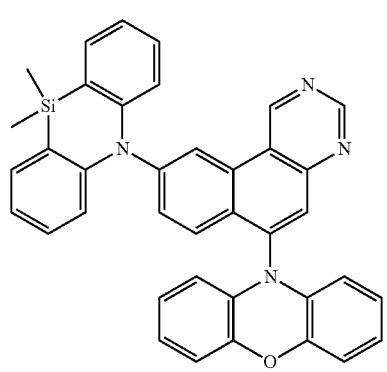
25
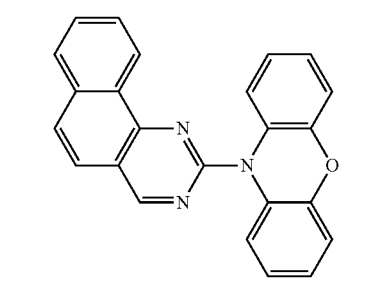
26
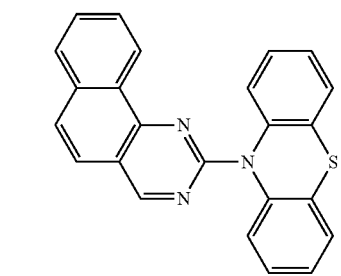
27
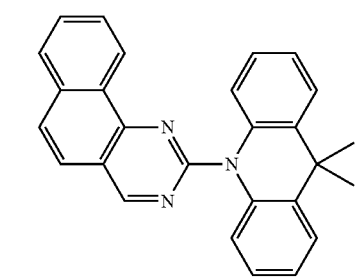
-continued
28
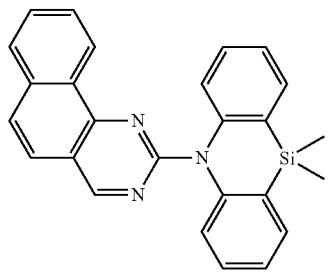
29
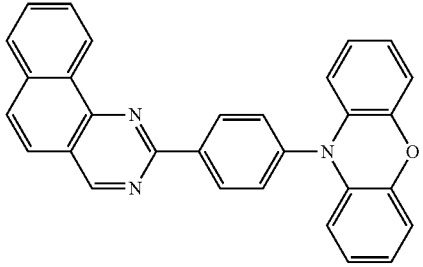
30
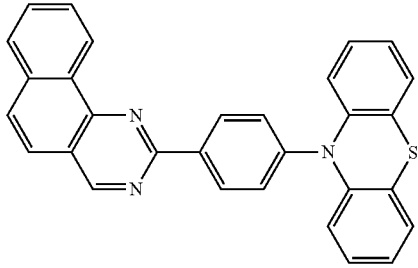
31
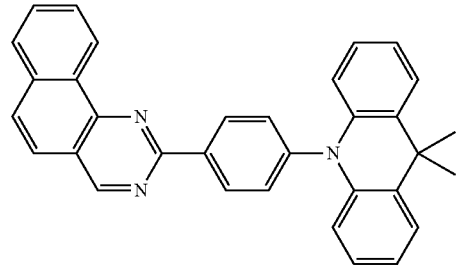
32
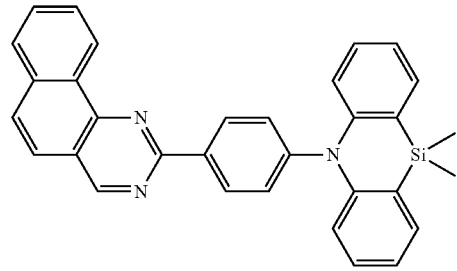

33
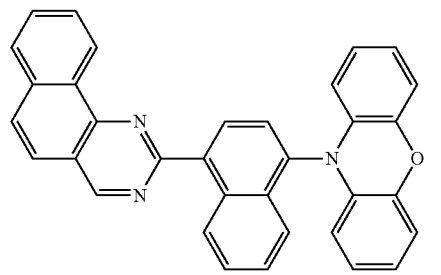
34
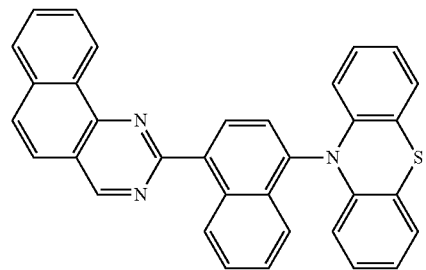
35
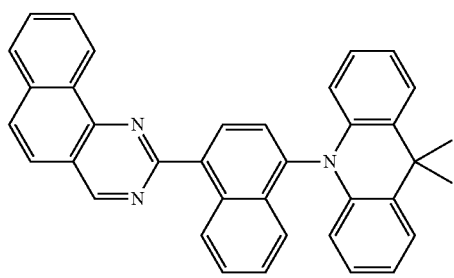
36
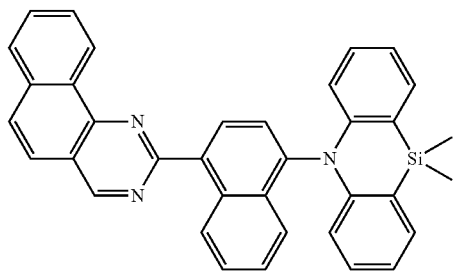
37
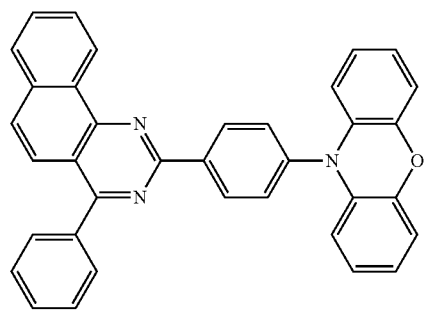
38
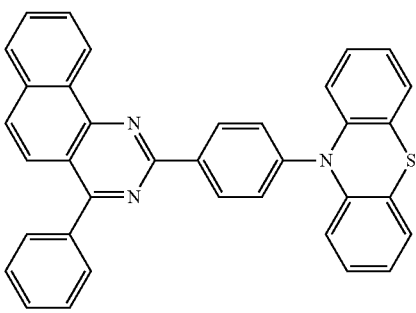
39
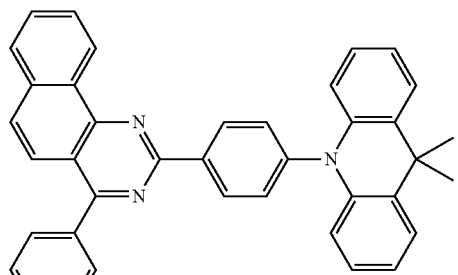
40
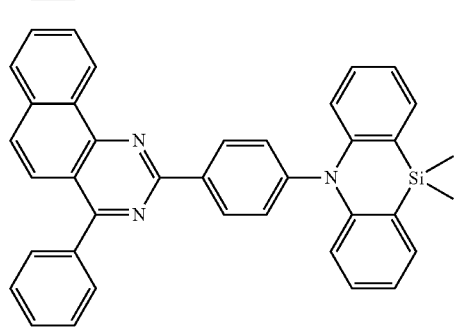
41
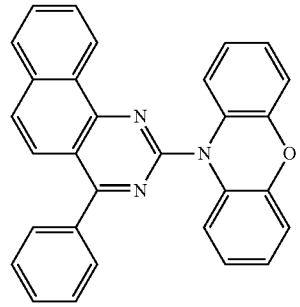
42
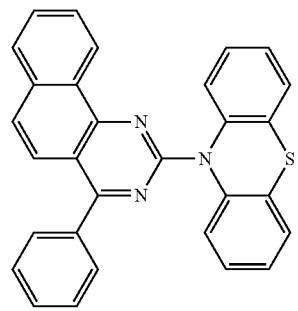

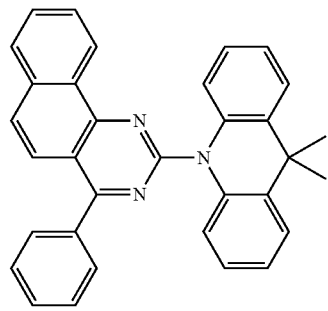
43
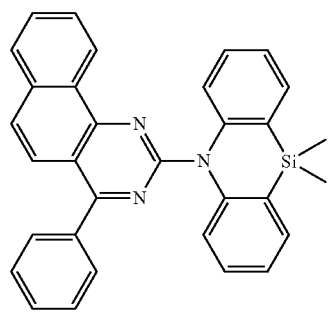
44
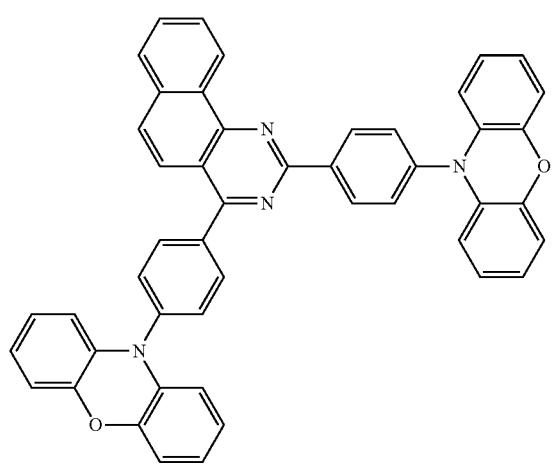
45
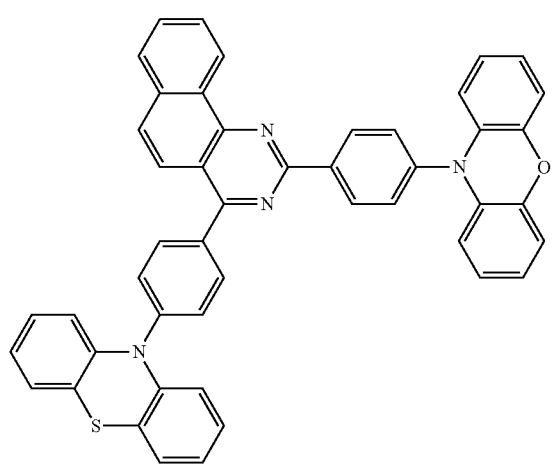
46
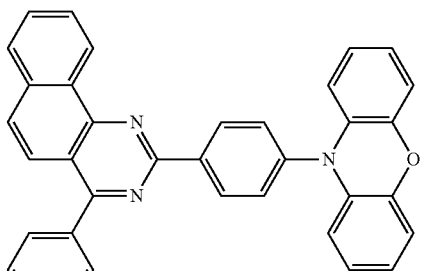
47
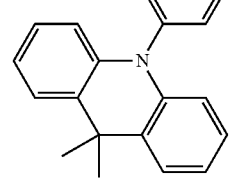
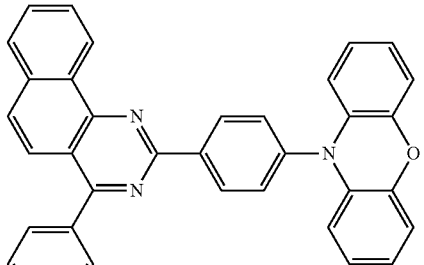
48
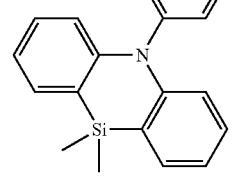
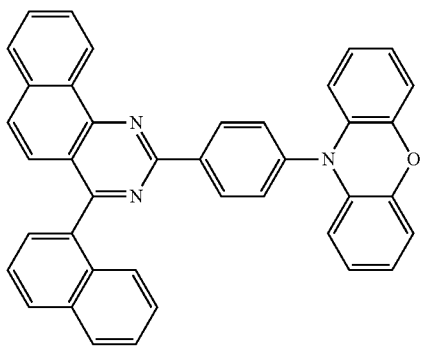
49

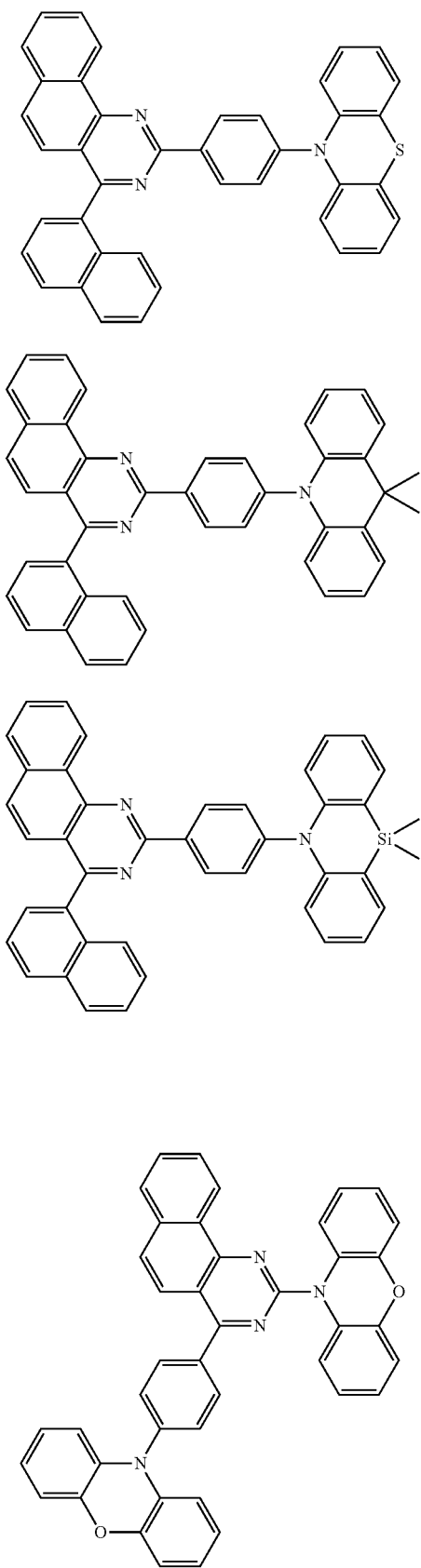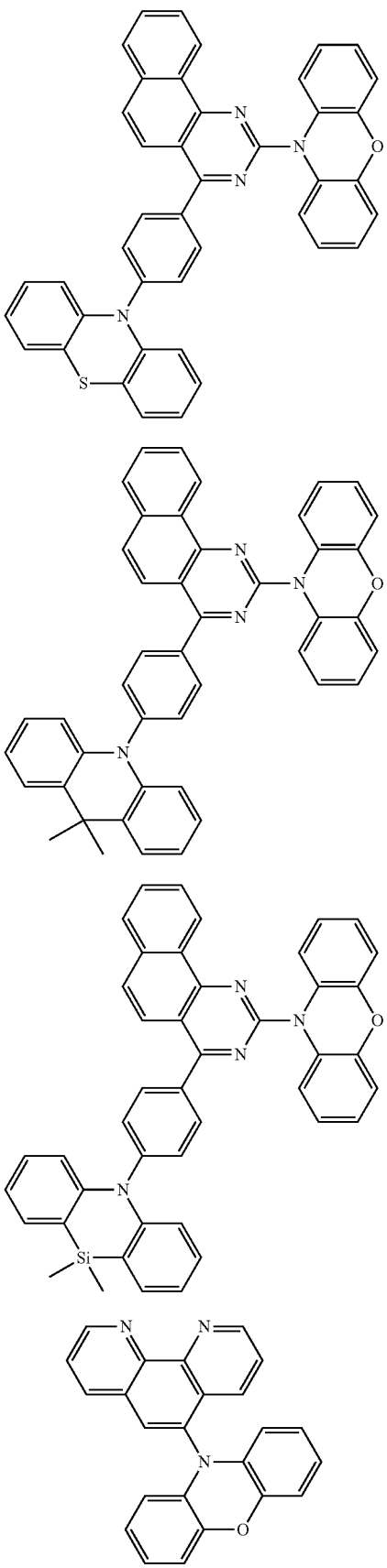

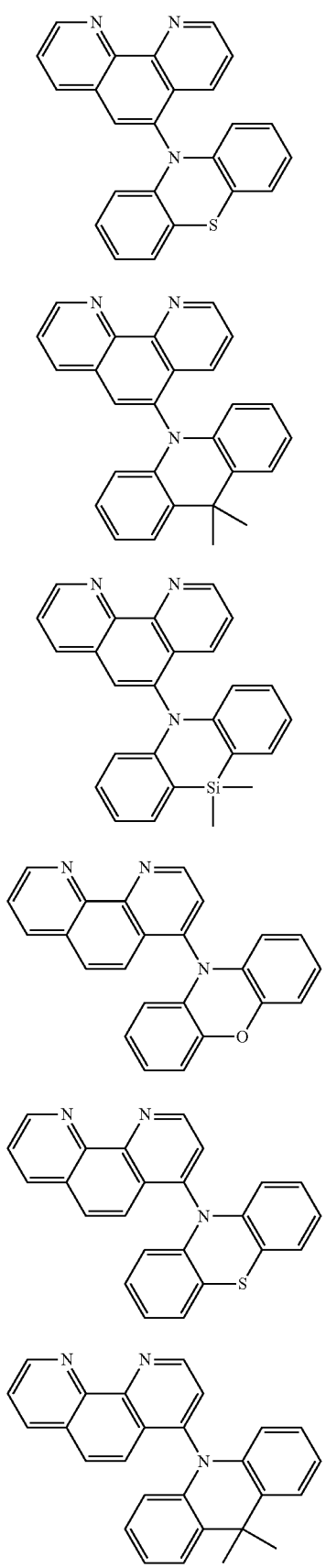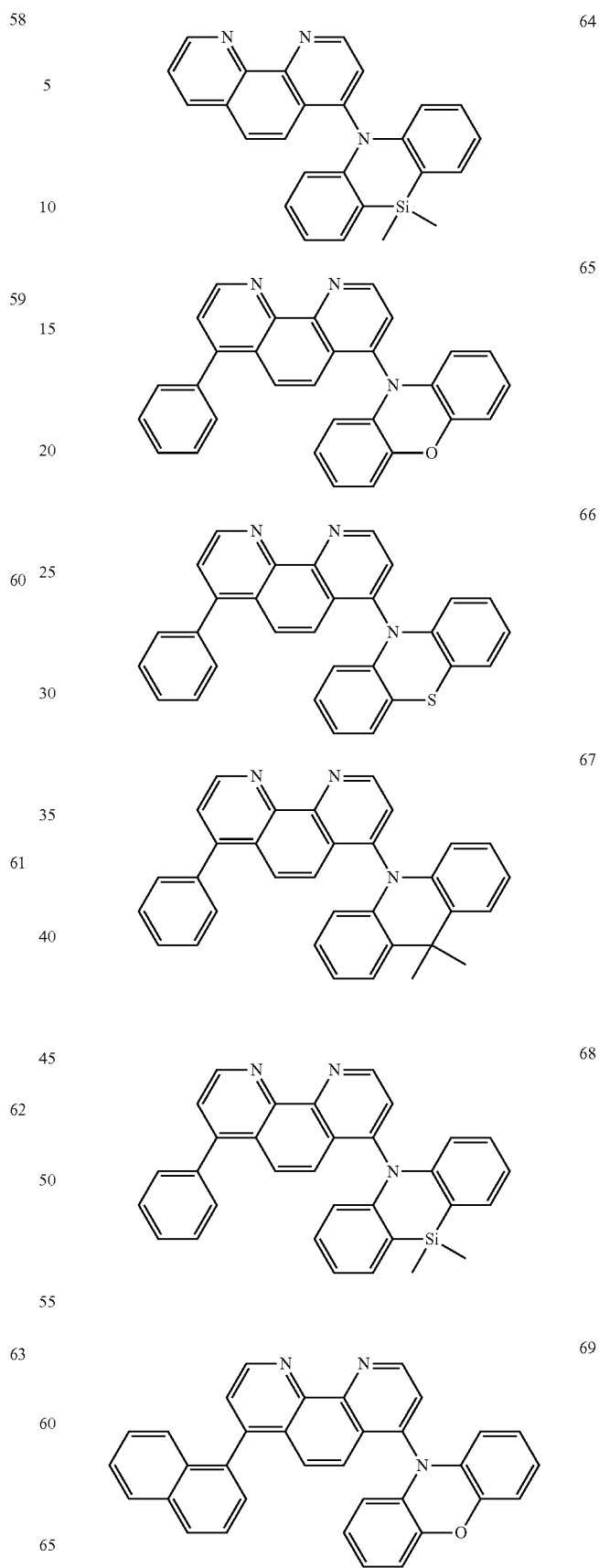

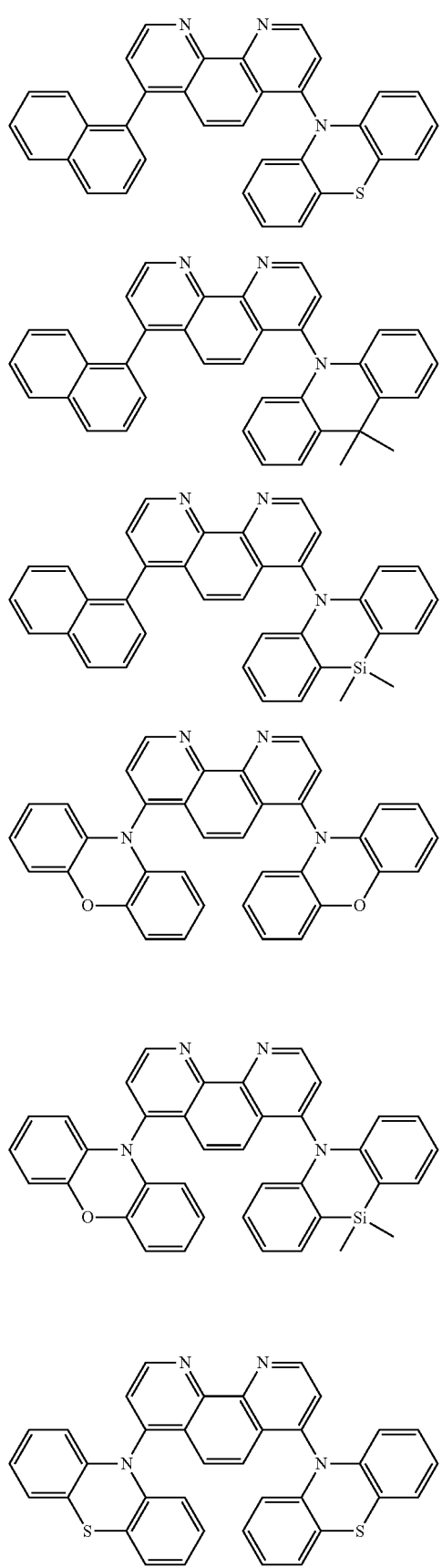
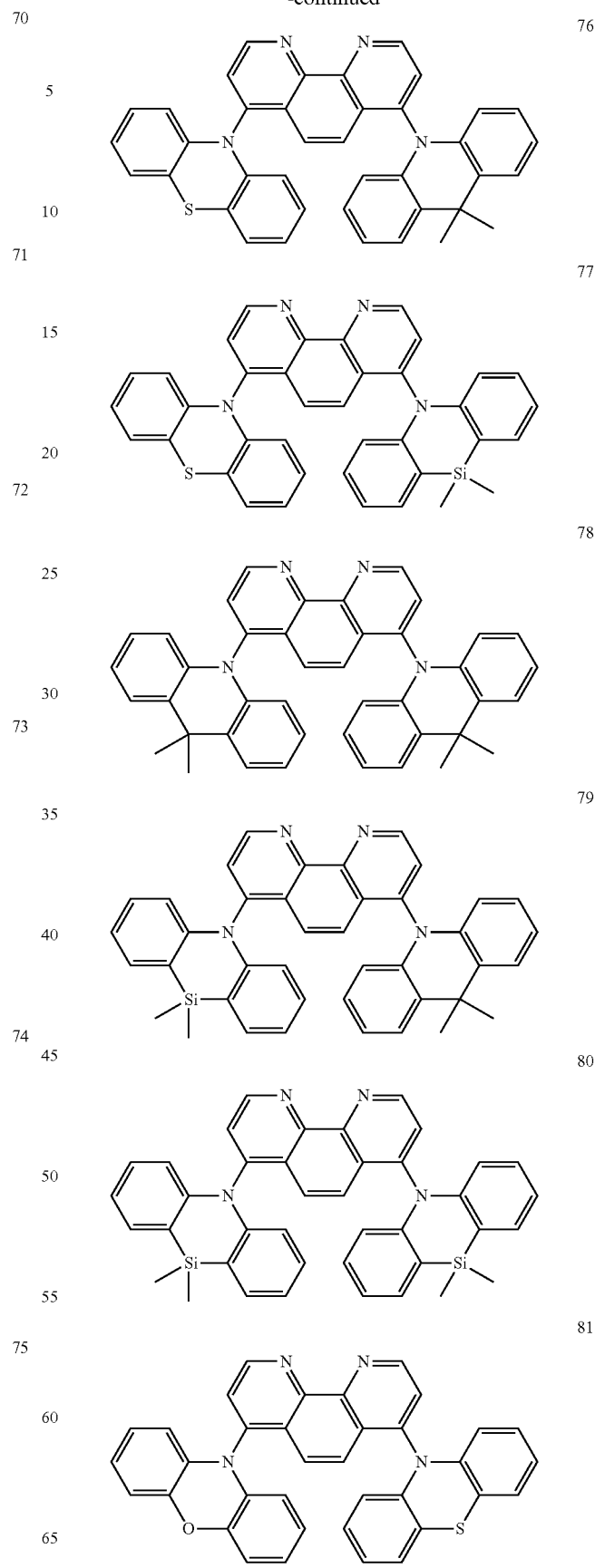

-continued
82
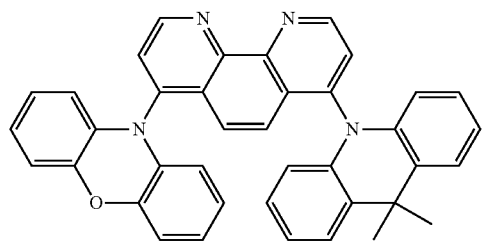
83
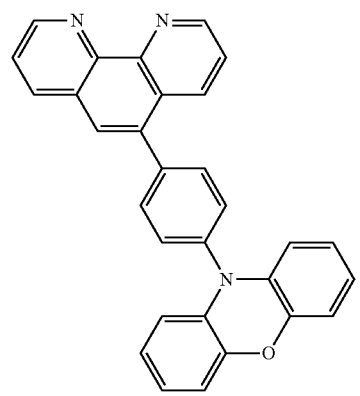
84
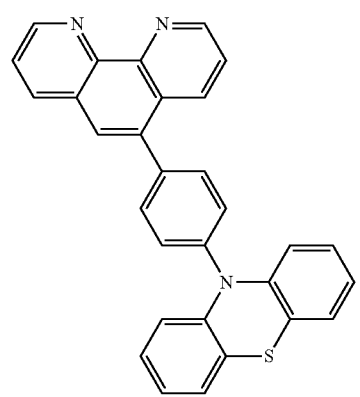
85
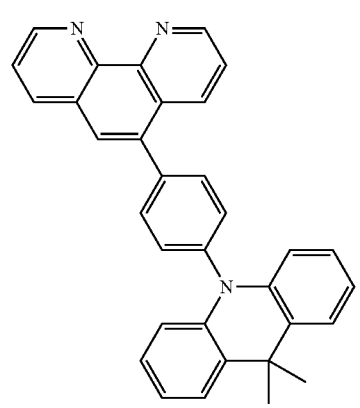
-continued
86
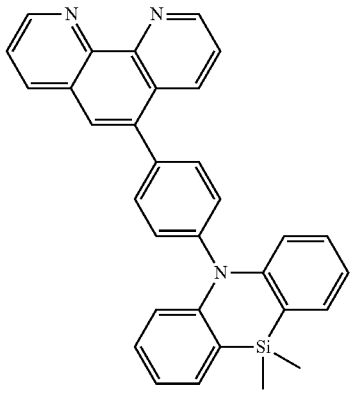
87
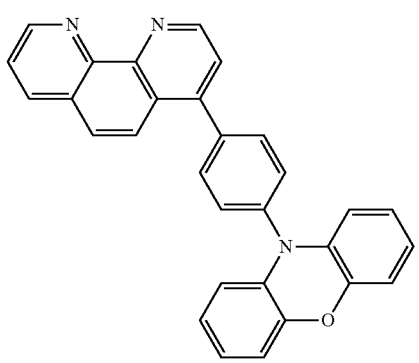
88
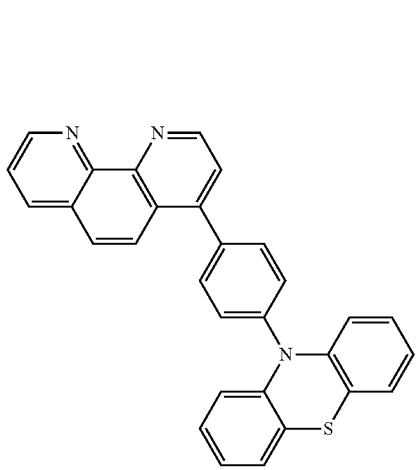
89
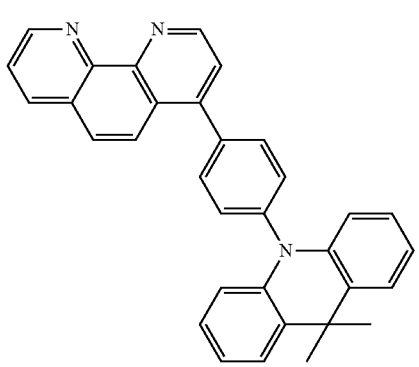

90
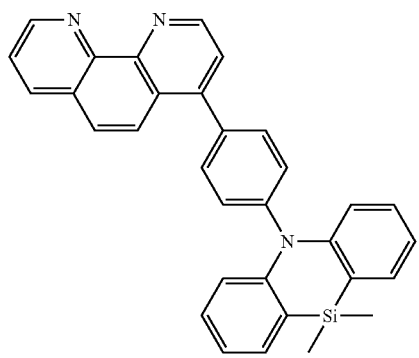
94
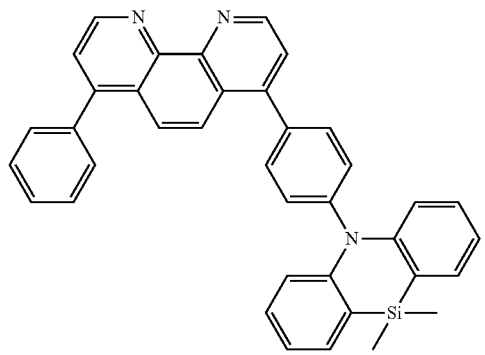
91
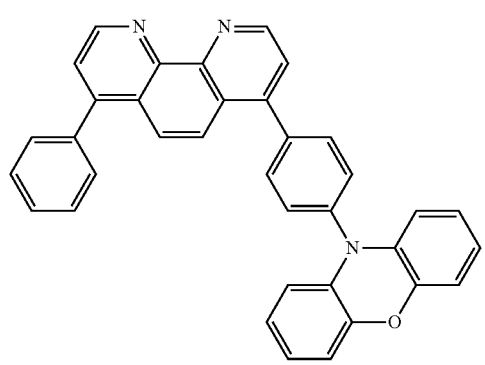
95
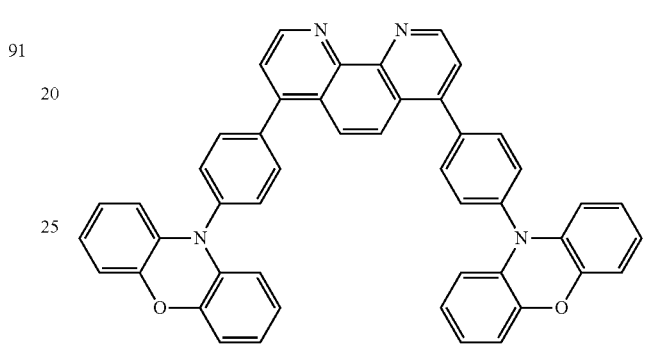
92
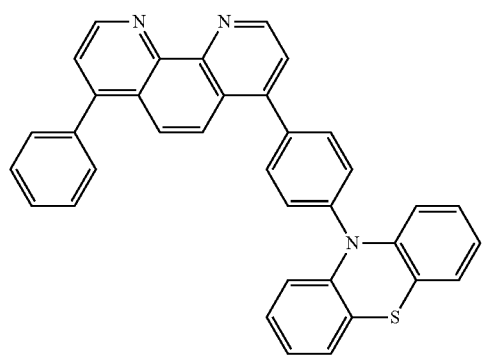
96
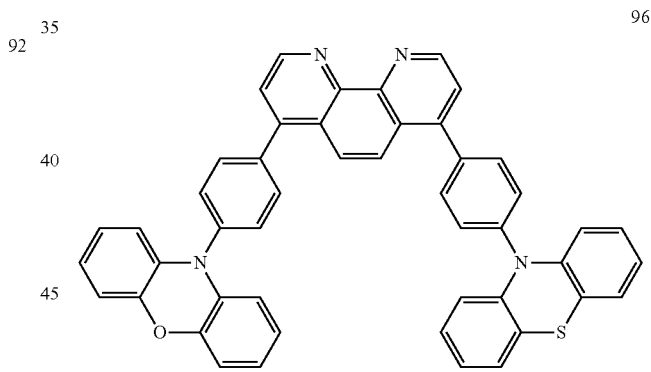
93
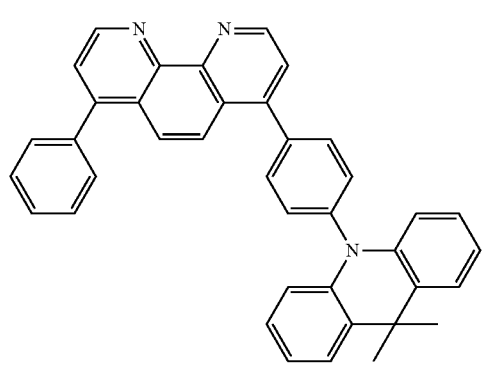
97
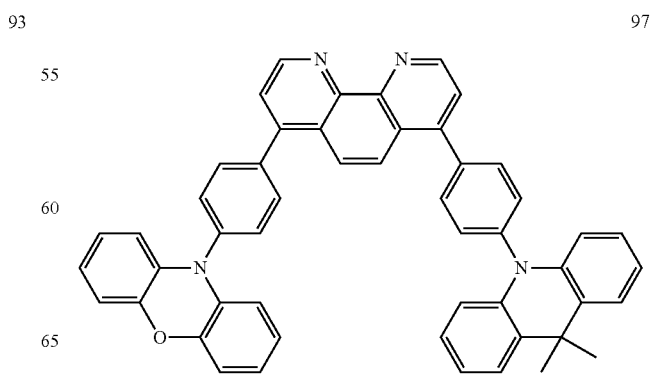

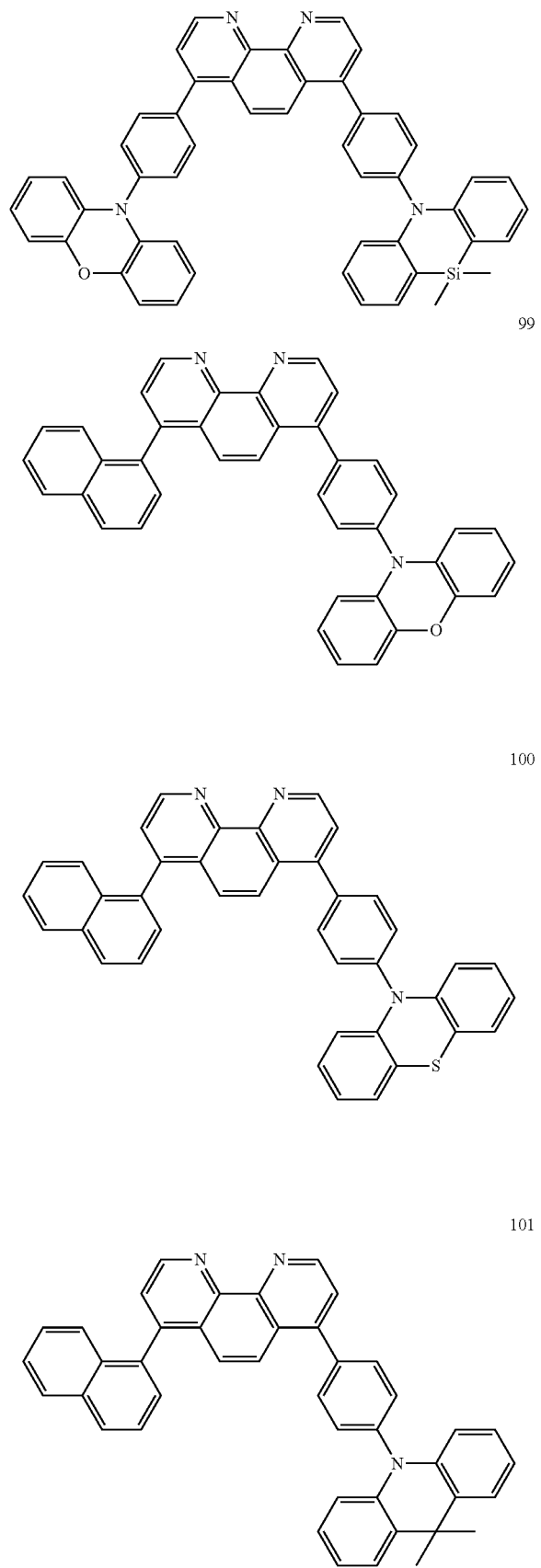
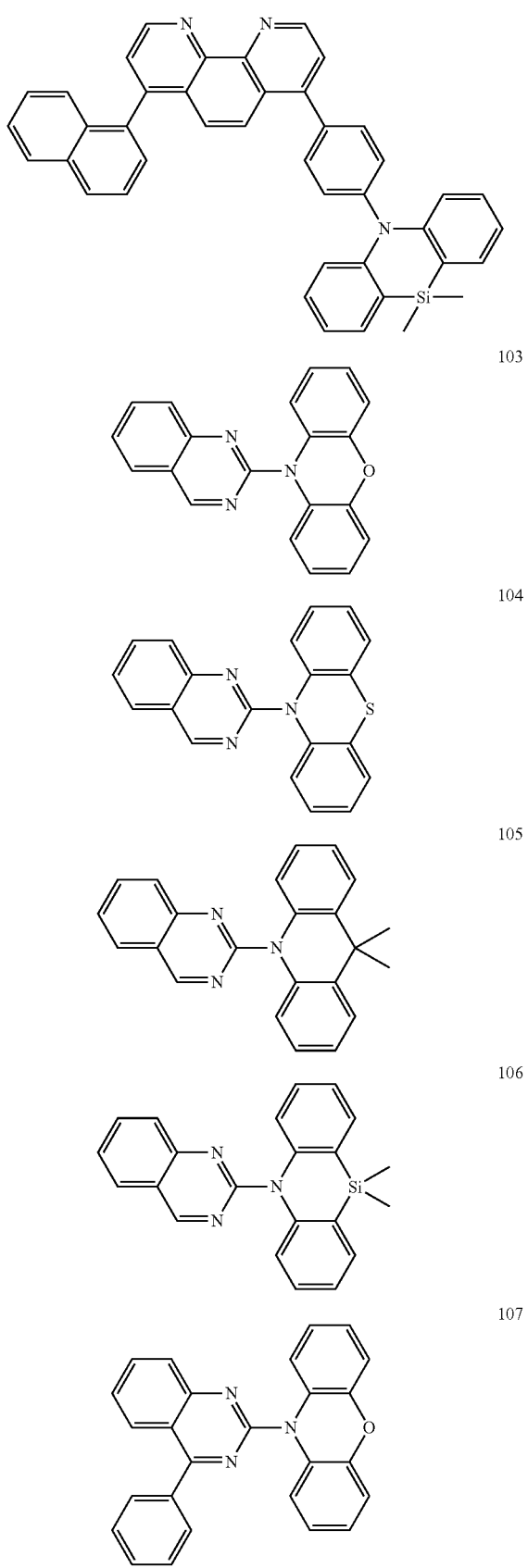

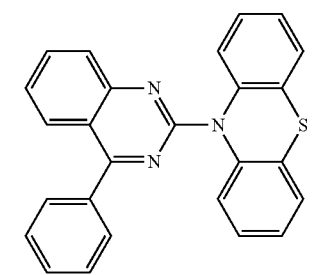
108
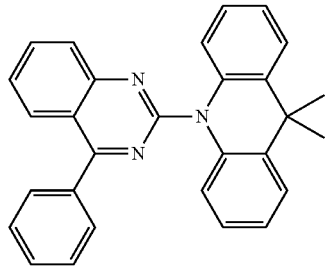
109
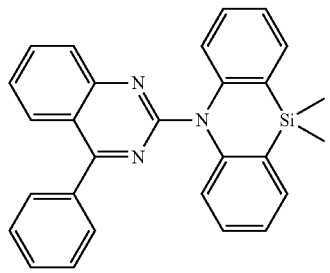
110
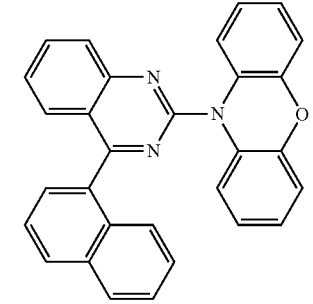
111
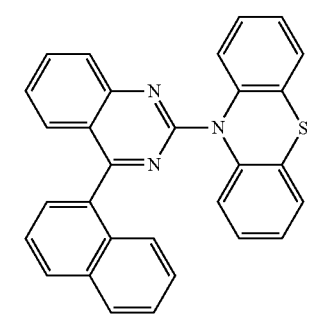
112
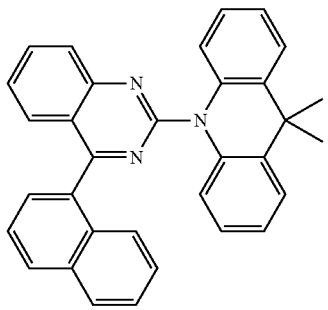
113
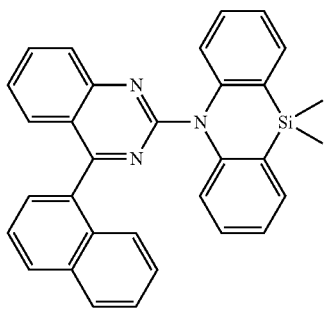
114
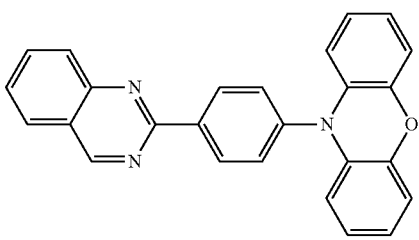
115
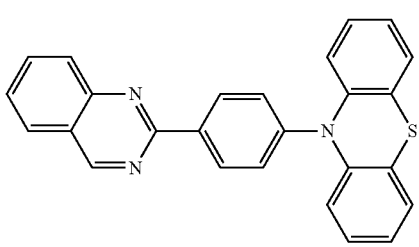
116
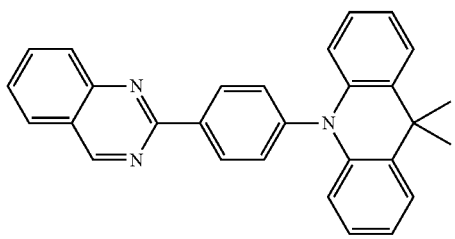
117
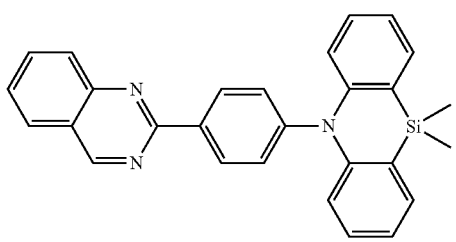
118

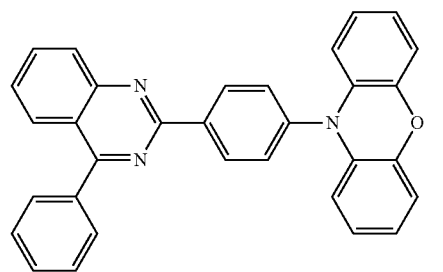
119
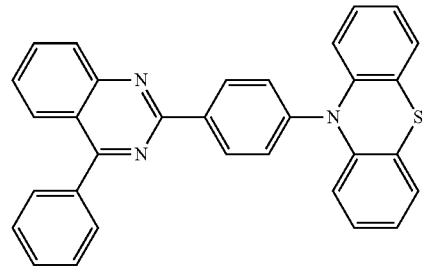
120
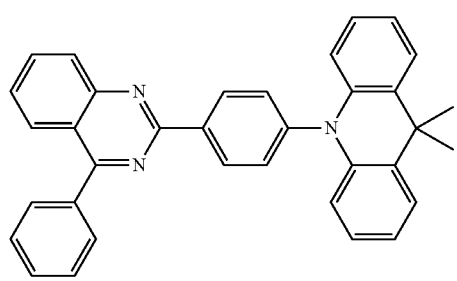
121
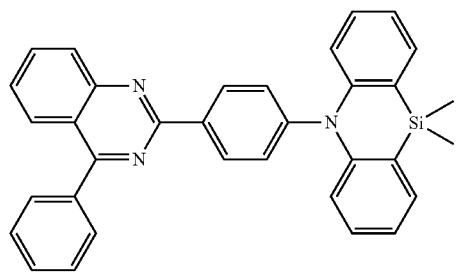
122
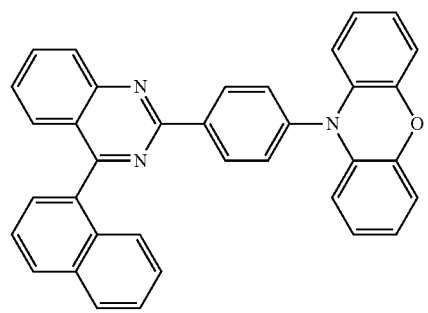
123
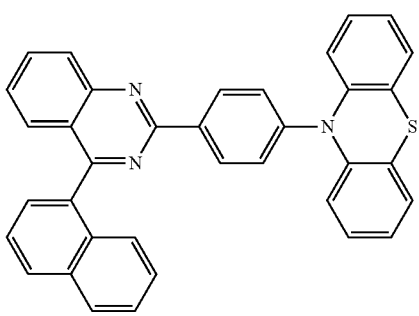
124
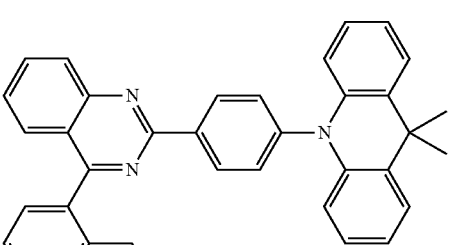
125
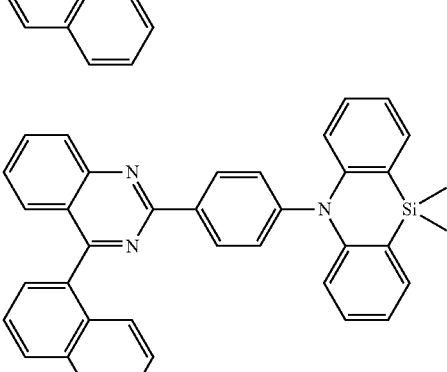
126
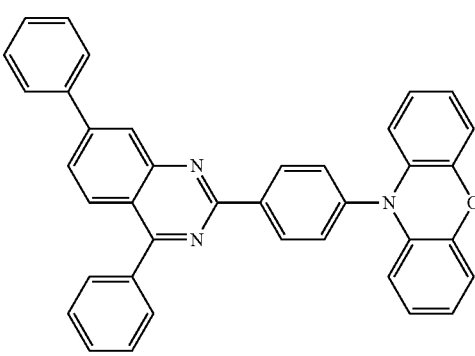
127
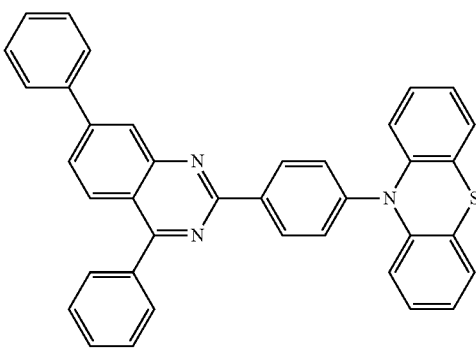
128

129
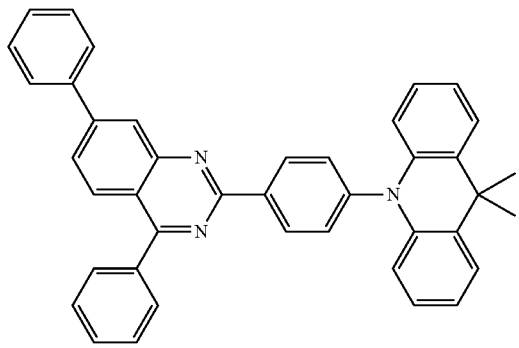
130
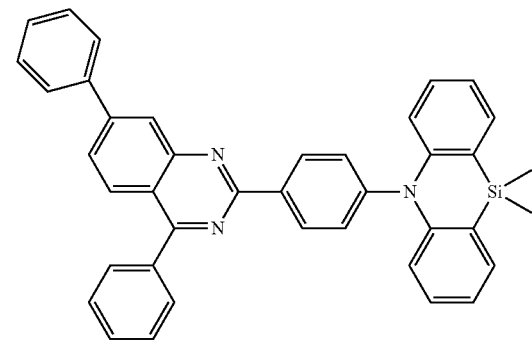
131
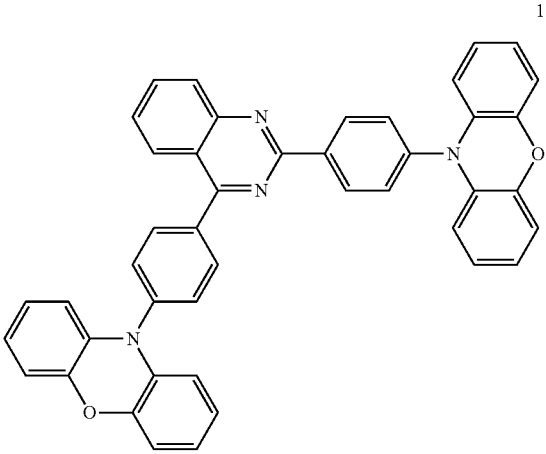
132
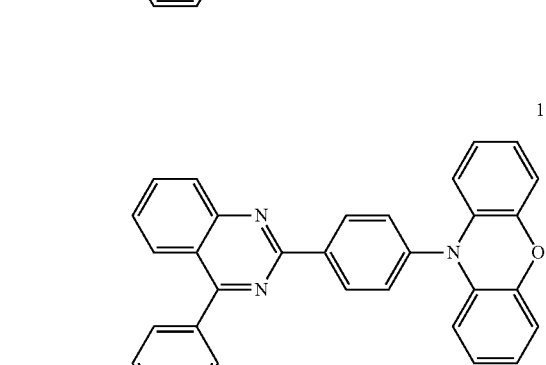
133
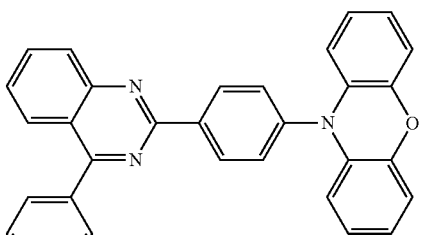
134
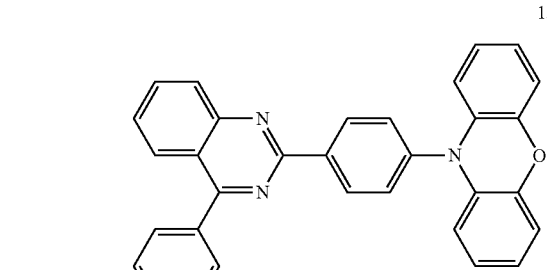
135
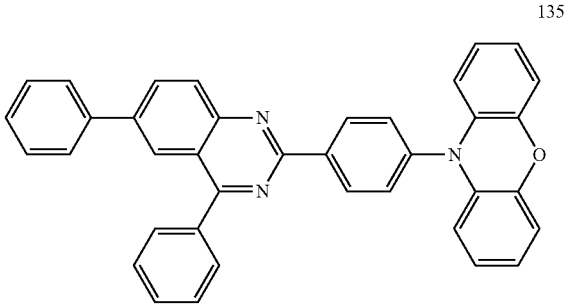
136
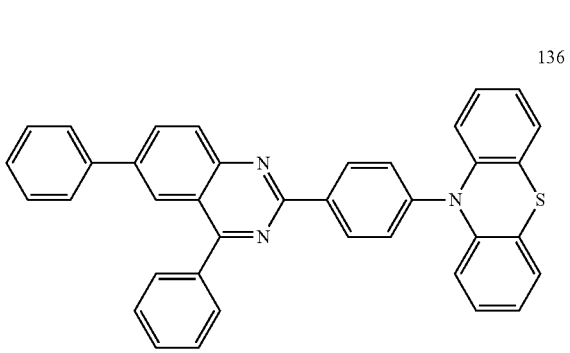

137
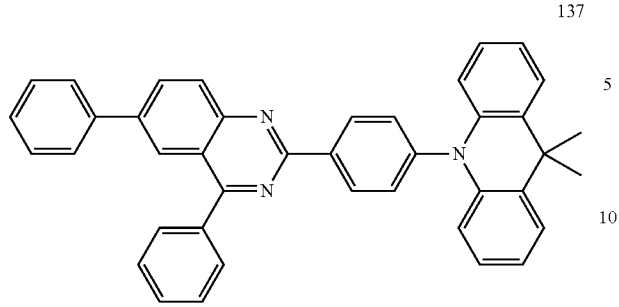
138
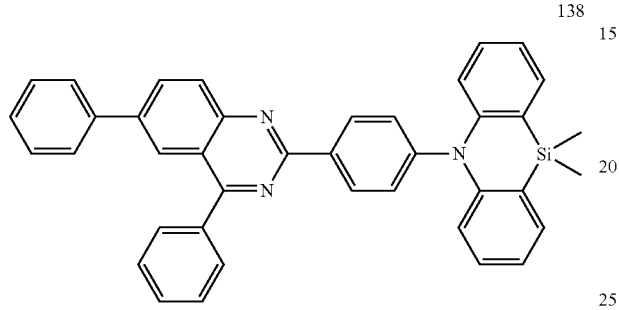
139
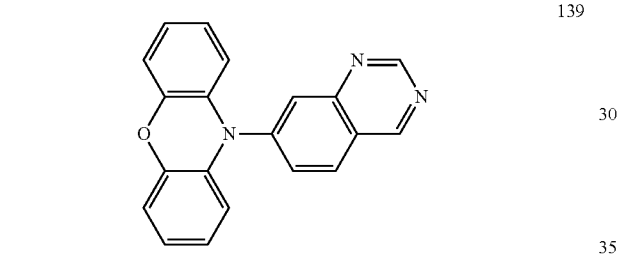
140
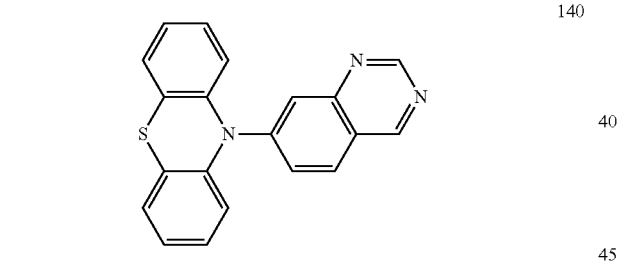
141
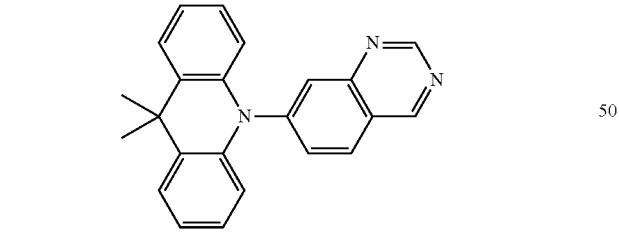
142
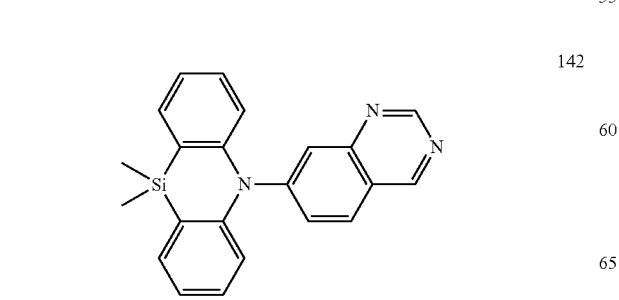
143
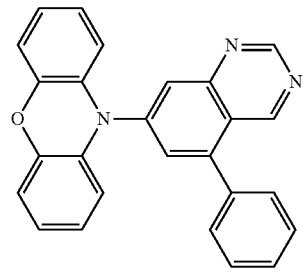
144
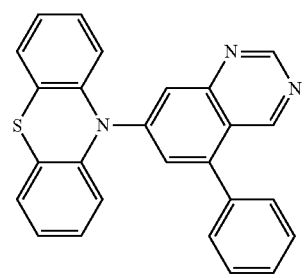
145
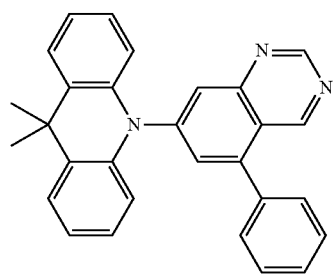
146
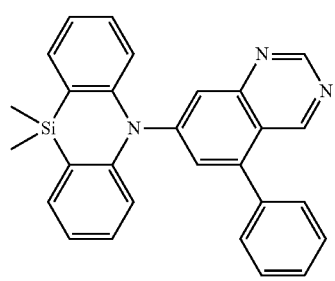
147
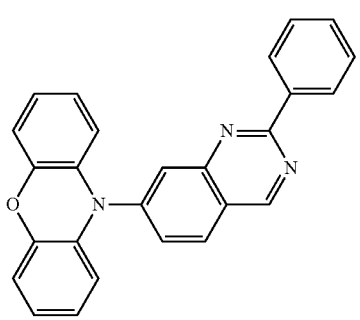

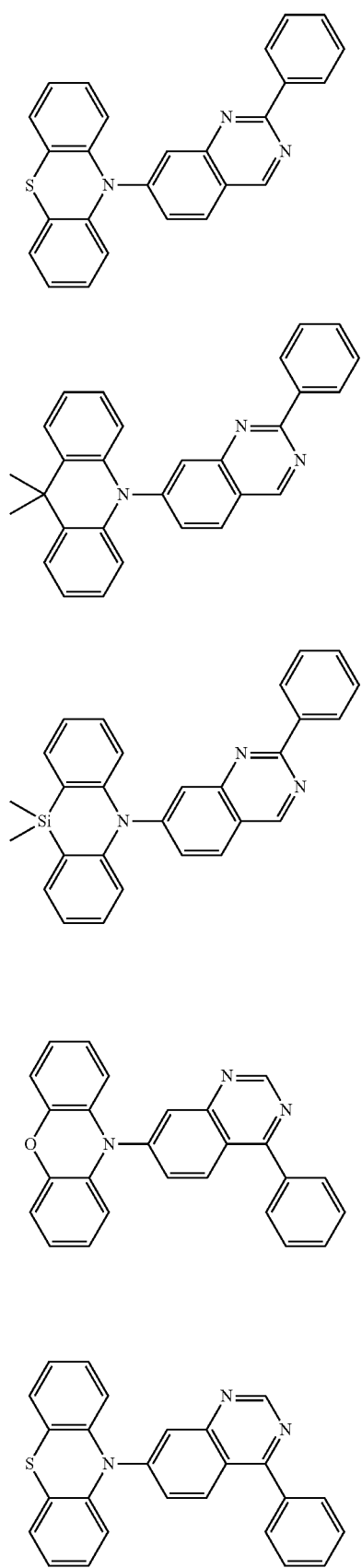
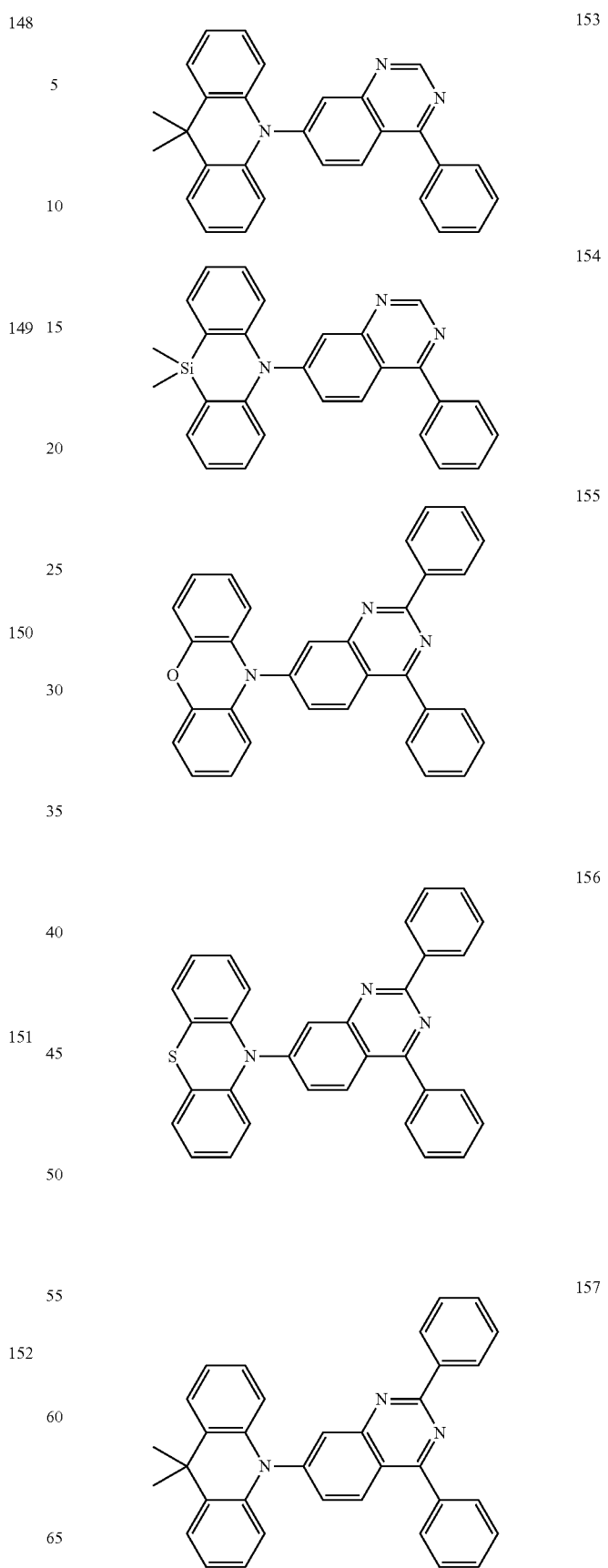

158
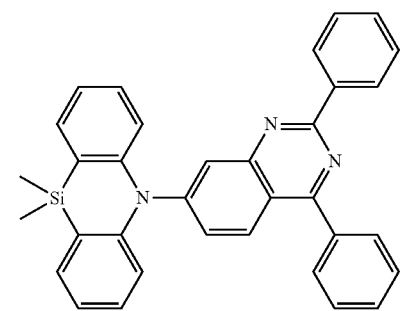
159
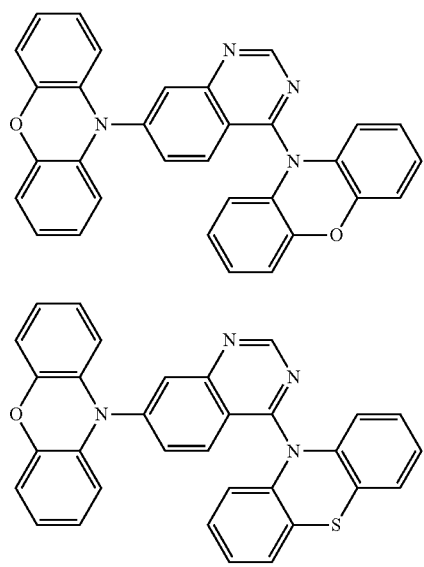
160
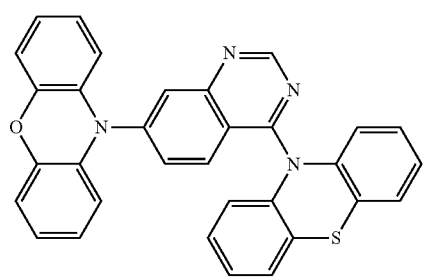
161
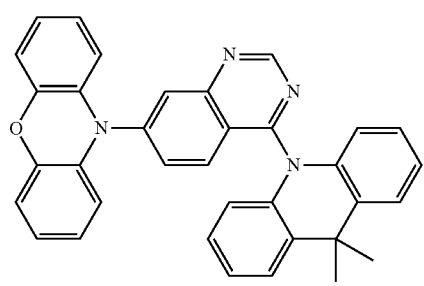
162
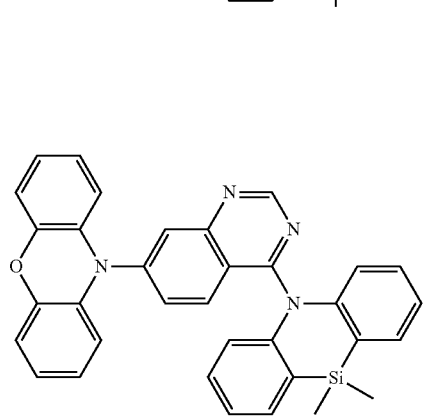
163
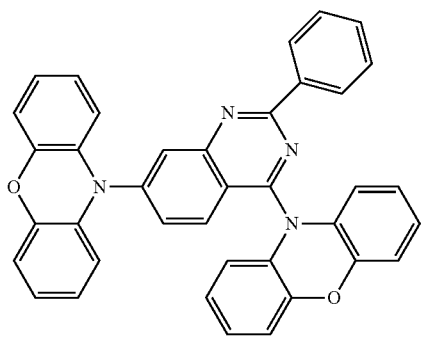
164
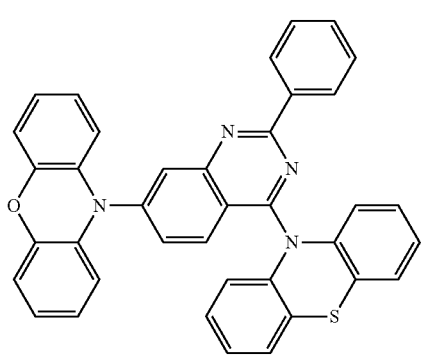
165
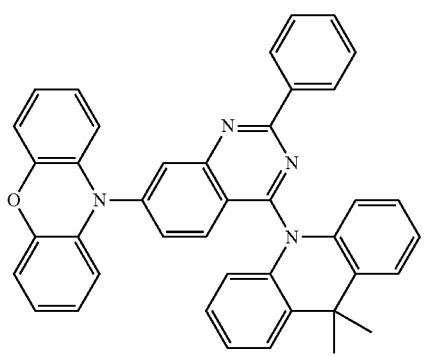
166
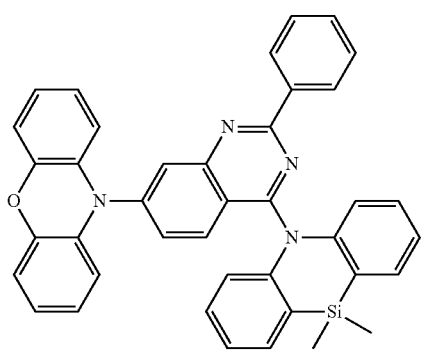

-continued
167
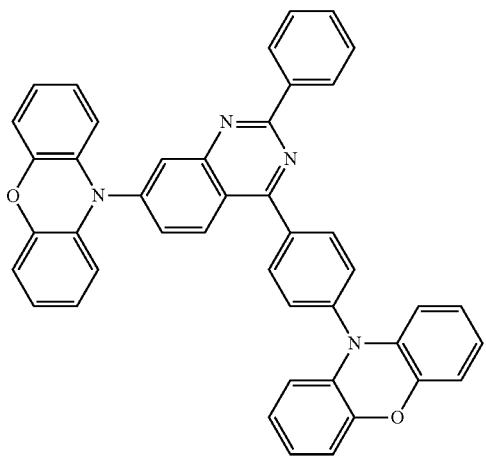
168
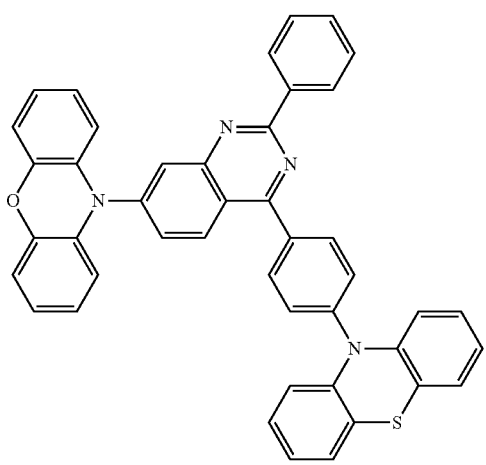
169
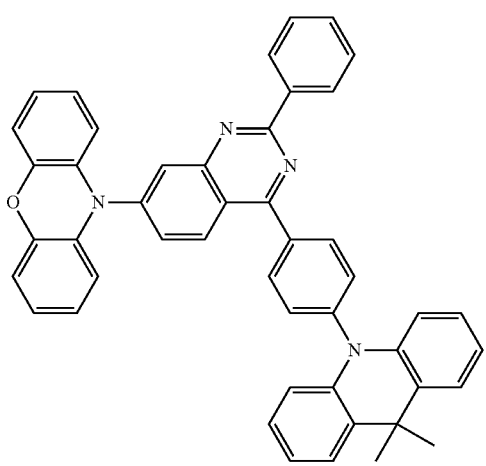
-continued
170
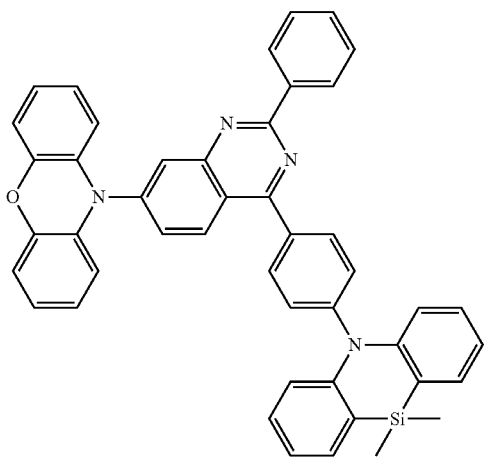
171
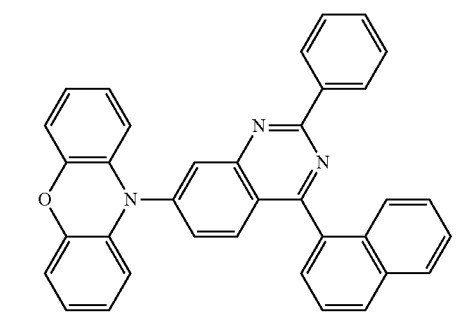
172
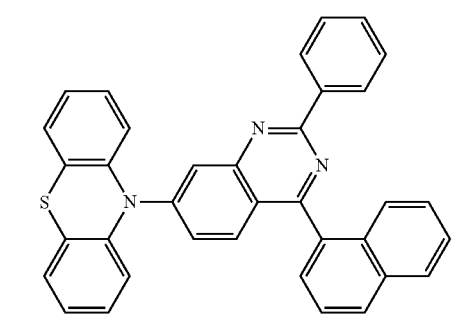
173
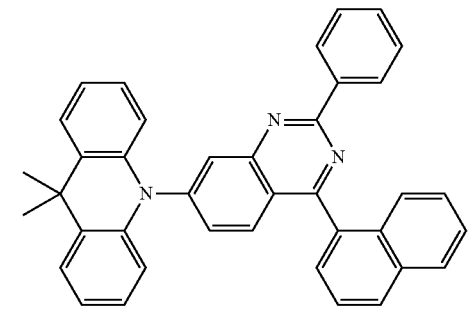

174
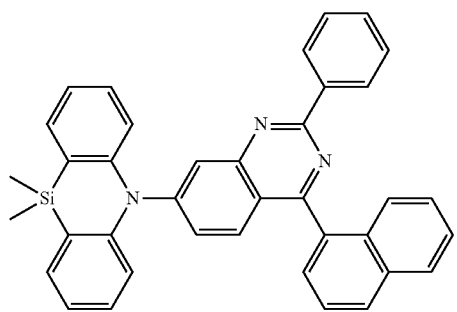
175
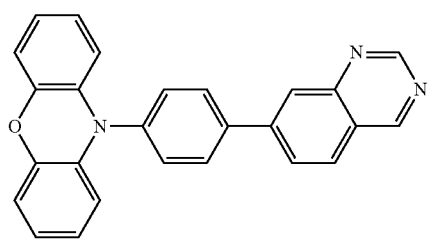
176
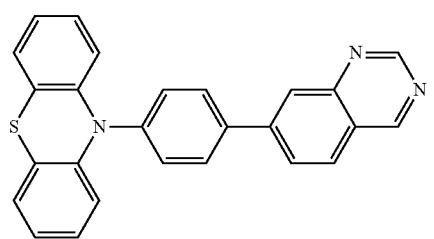
177
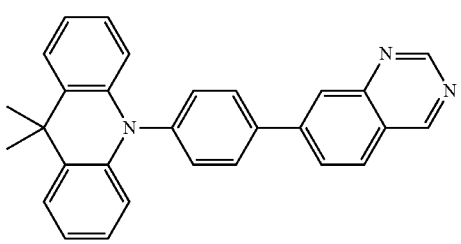
178
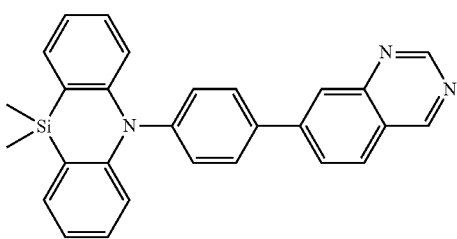
179
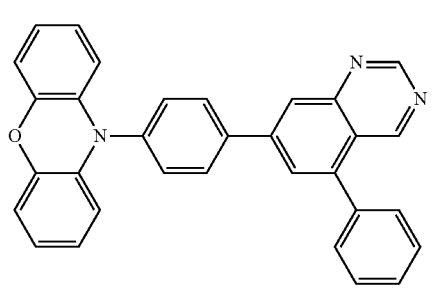
180
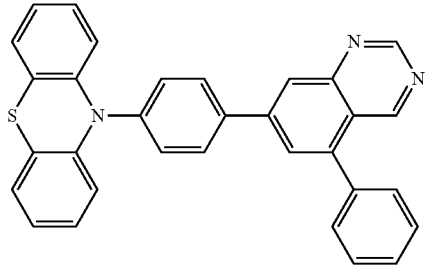
181
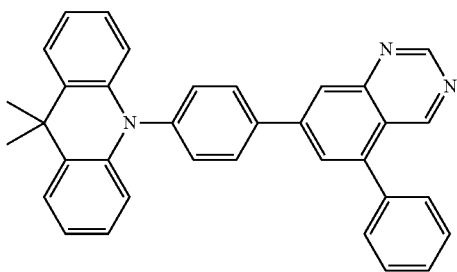
182
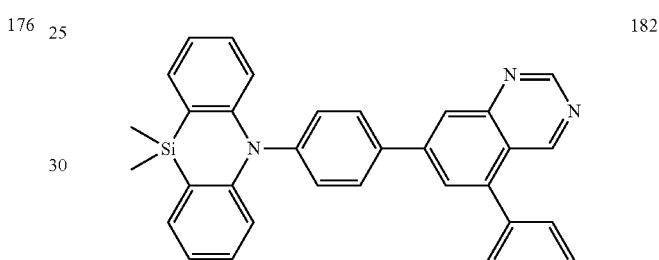
183
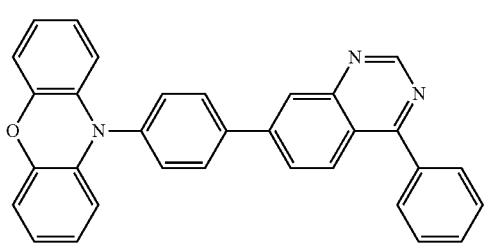
184
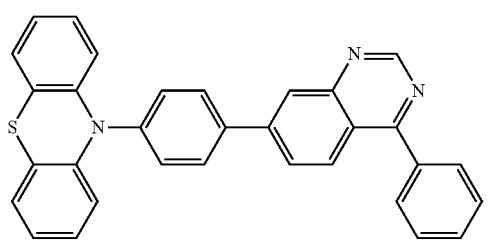
185
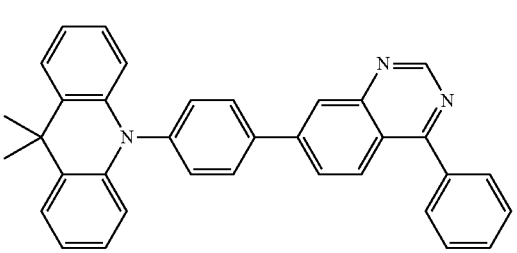

186
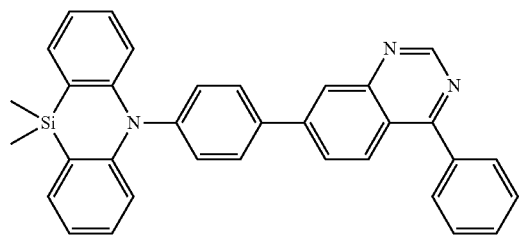
187
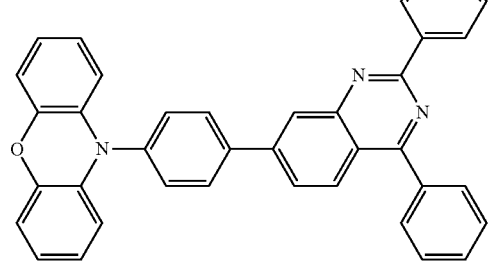
188
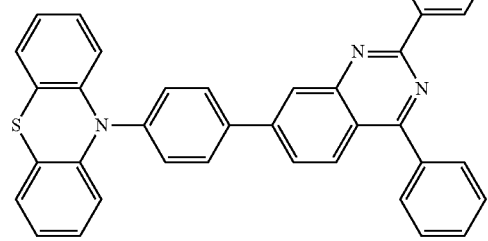
189
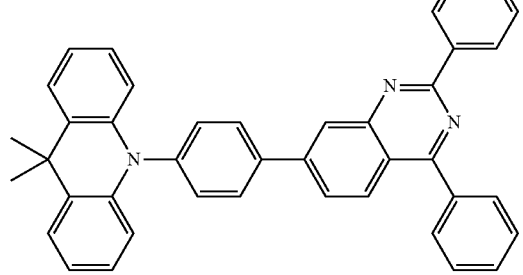
190
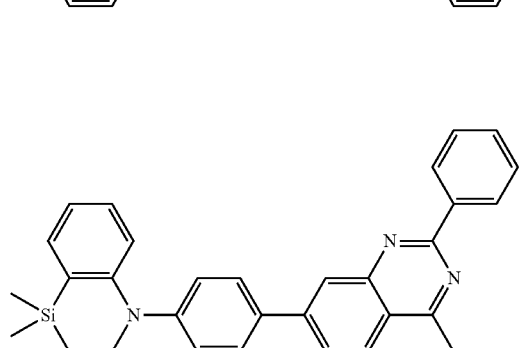
191
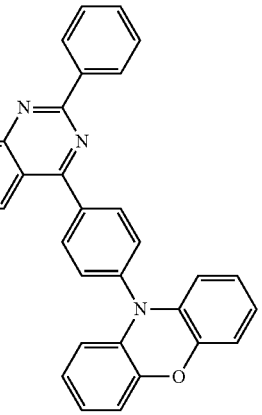
192
193
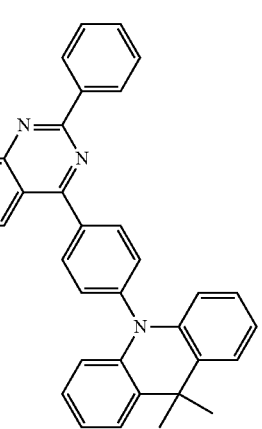

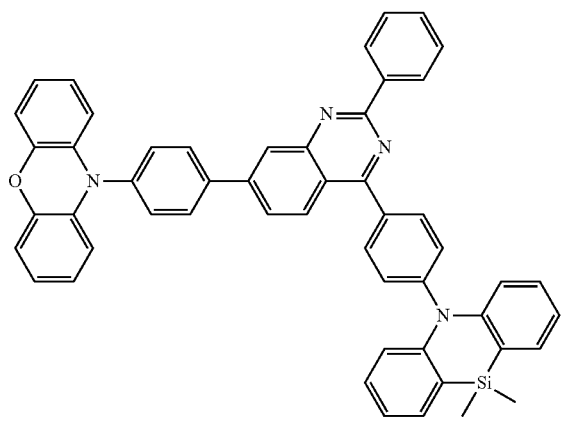

194

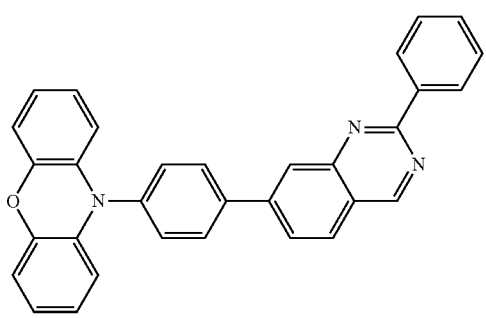

195

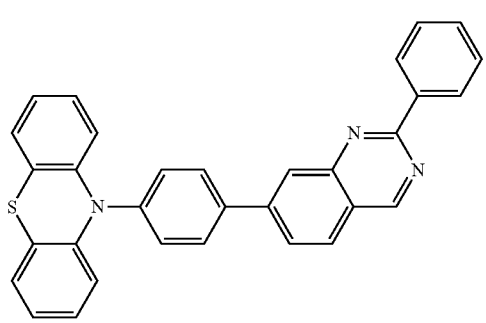

196

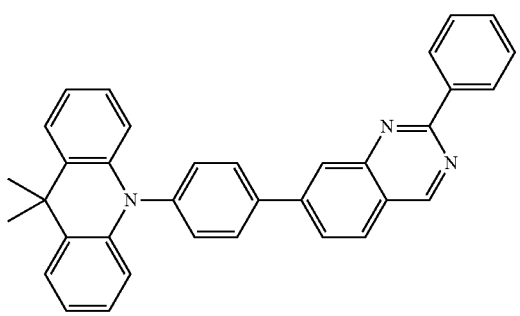

197

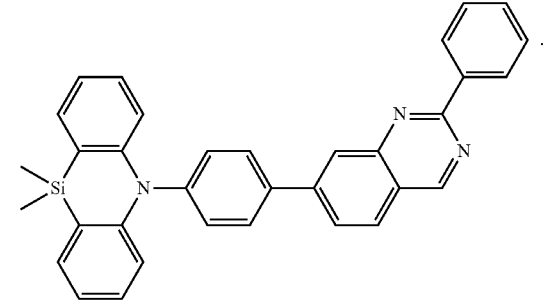

198

In one embodiment, the energy difference between the lowest singlet excited state ($S_1$) and the lowest triplet excited state ($T_1$) in the disclosed compounds may be configured to be $\Delta E_{st} \leq 0.30$ eV.

In another embodiment, the energy difference between the lowest singlet excited state ($S_1$) and the lowest triplet excited state ($T_1$) in the disclosed compounds may be configured to be $\Delta E_{st} \leq 0.25$ eV.

In another embodiment, the energy difference between the lowest singlet excited state ($S_1$) and the lowest triplet excited state ($T_1$) in the disclosed compounds may be configured to be $\Delta E_{st} \leq 0.20$ eV.

In another embodiment, the energy difference between the lowest singlet excited state ($S_1$) and the lowest triplet excited state ($T_1$) in the disclosed compounds may be configured to be $\Delta E_{st} \leq 0.15$ eV.

In another embodiment, the energy difference between the lowest singlet excited state ($S_1$) and the lowest triplet excited state ($T_1$) in the disclosed compounds may be configured to be $\Delta E_{st} \leq 0.10$ eV.

In another embodiment, the energy difference between the lowest singlet excited state ($S_1$) and the lowest triplet excited state ($T_1$) in the disclosed compounds may be configured to be $\Delta E_{st} \leq 0.05$ eV.

In another embodiment, the energy difference between the lowest singlet excited state ($S_1$) and the lowest triplet excited state ($T_1$) in the disclosed compounds may be configured to be $\Delta E_{st} \leq 0.02$ eV.

In another embodiment, the energy difference between the lowest singlet excited state ($S_1$) and the lowest triplet excited state ($T_1$) in the disclosed compounds may be configured to be $\Delta E_{st} \leq 0.01$ eV.

In the disclosed compounds, the energy difference between the lowest singlet excited state ($S_1$) and the lowest triplet excited state ($T_1$) may be configured to be $\Delta E_{st} = E_{S1} - E_{T1} \leq 0.30$ eV, or even less than or equal to 0.02 eV, such that the disclosed compounds may be used as TADF materials for the organic optoelectronic devices to improve the luminous efficiency. Moreover, the disclosed compounds may not contain expensive metal complexes, thereby reducing the manufacturing cost and widening the applications.

The present discourse also provides an organic optoelectronic device. The organic optoelectronic device may include an OLED, an organic solar cell, an organic photoelectric sensor, an organic storage device and any other appropriate organic optoelectronic devices. In one embodiment, the organic optoelectronic device may be an OLED. The OLED may include an anode, a cathode, and one or more organic thin film layers disposed between the anode and the cathode. At least one of the organic thin film layers may be a light-emitting layer, and the light-emitting layer may comprise any of the disclosed compounds of the present disclosure. The disclosed compound may be used as a dopant material, a co-doping material, or a host material in the light-emitting layer.

In certain embodiments, the OLED may also include at least one or a combination of at least two of a hole transport layer (HTL), a hole injection layer (HIL), an electron blocking layer (EBL), a hole blocking layer (HBL), an electron transport layer (ETL), an electron injection layer (EIL). At least one of the hole transport layer (HTL), the hole injection layer (HIL), the electron blocking layer (EBL), the hole blocking layer (HBL), the electron transport layer (ETL), the electron injection layer (EIL) may comprise any of the disclosed compounds, in which the disclosed compound may be used as a dopant material, a co-doping material, or a host material.

FIG. 1 illustrates a schematic diagram of an exemplary OLED consistent with disclosed embodiments. As shown in FIG. 1, the OLED may include an anode 110 and a cathode 120 disposed on a substrate layer 100. At least a light-emitting layer 130 may be disposed between the anode 110 and the cathode 120. Other appropriate components may also be included. Electrons and holes may be recombined in the light-emitting layer 130, such that light is emitted from light-emitting layer 130.

Figure 2:
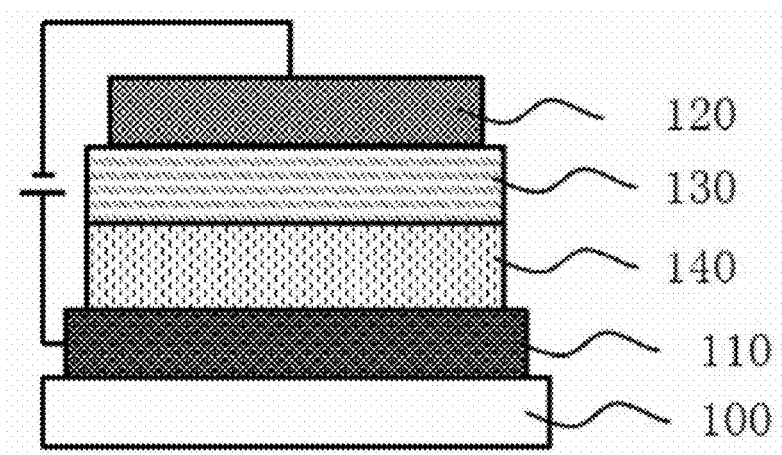
FIG. 2 illustrates a schematic diagram of another exemplary OLED consistent with disclosed embodiments.

FIG. 2 illustrates a schematic diagram of another exemplary OLED consistent with disclosed embodiments. The similarities between FIG. 1 and FIG. 2 are not repeated here, while certain difference may be explained. As shown in FIG. 2, a hole transport layer (HTL) 140 and a light-emitting layer 130 may be disposed between the anode 110 and the cathode 120. The hole transport layer (HTL) 140 may transfer the holes to the light-emitting layer 130.

Figure 3:
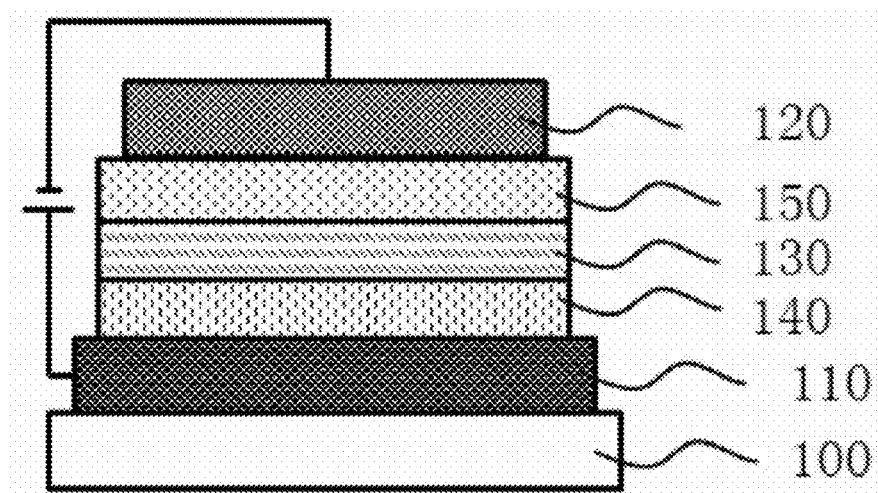
FIG. 3 illustrates a schematic diagram of another exemplary OLED consistent with disclosed embodiments.

FIG. 3 illustrates a schematic diagram of another exemplary OLED consistent with disclosed embodiments. The similarities between FIG. 1 and FIG. 3 are not repeated here, while certain difference may be explained. As shown in FIG. 3, a hole transport layer (HTL) 140, a light-emitting layer 130 and an electron transport layer (ETL) 150 may be disposed between the anode 110 and the cathode 120. The electron transport layer (ETL) 150 may transfer the electrons to the light-emitting layer 130.

Figure 4:
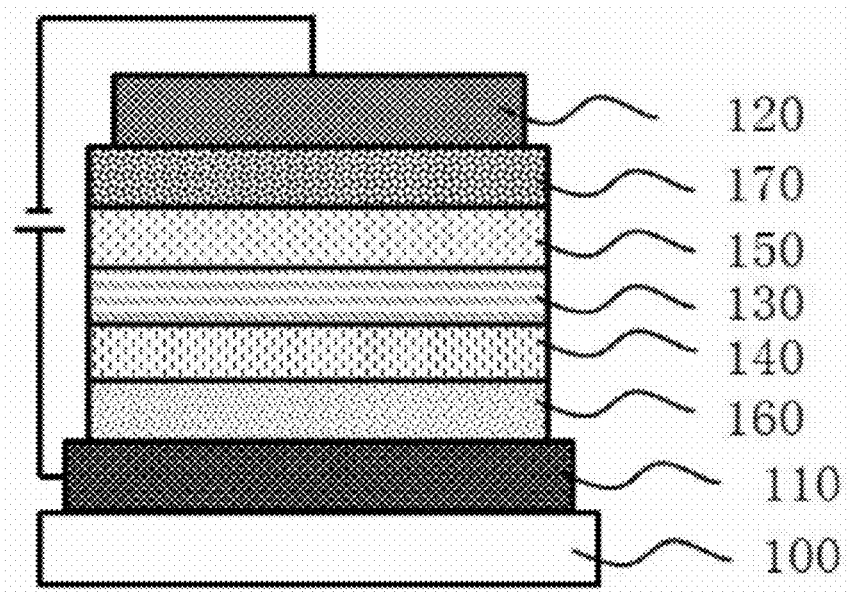
FIG. 4 illustrates a schematic diagram of another exemplary OLED consistent with disclosed embodiments.

FIG. 4 illustrates a schematic diagram of another exemplary OLED consistent with disclosed embodiments. The similarities between FIG. 1 and FIG. 4 are not repeated here, while certain difference may be explained. As shown in FIG. 4, a hole injection layer (HIL) 160, a hole transport layer (HTL) 140, a light-emitting layer 130, an electron transport layer (ETL) 150, and an electron injection layer (EIL) 170 may be disposed between the anode 110 and the cathode 120. The hole injection layer (HIL) 160 may improve the ability to transfer holes from the anode to the organic thin film layers. The electron injection layer (EIL) 170 may improve the ability to transfer electrons from the cathode to the organic thin film layers to reduce the driving voltage of the OLED.

Figure 5:
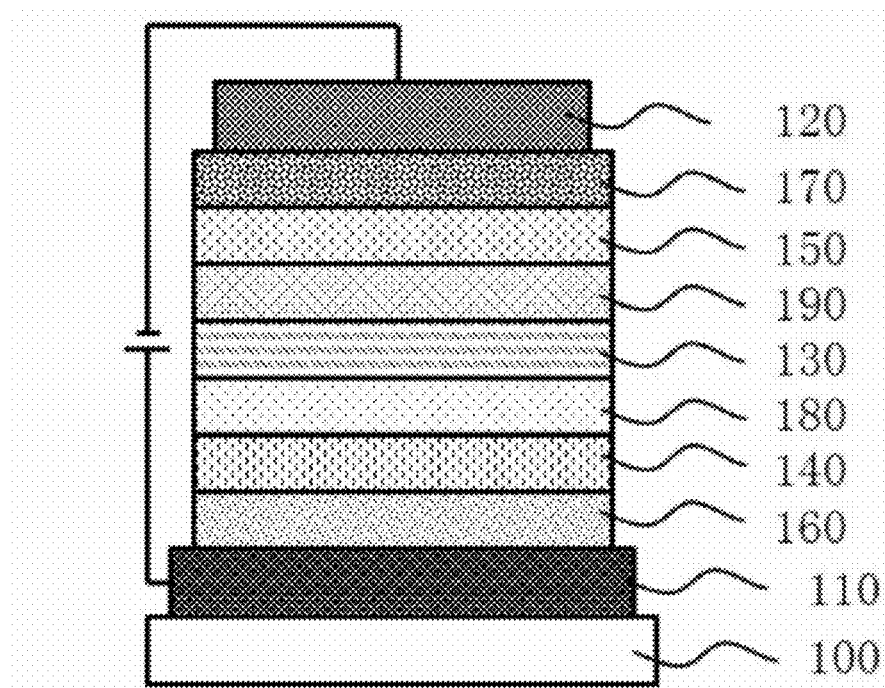
FIG. 5 illustrates a schematic diagram of another exemplary OLED consistent with disclosed embodiments.

FIG. 5 illustrates a schematic diagram of another exemplary OLED consistent with disclosed embodiments. The similarities between FIG. 1 and FIG. 5 are not repeated here, while certain difference may be explained. As shown in FIG. 5, a hole injection layer (HIL) 160, a hole transport layer (HTL) 140, an electron blocking layer (EBL) 180, a light-emitting layer 130, a hole blocking layer (HBL) 190, an electron transport layer (ETL) 150, and an electron injection layer (EIL) 170 may be disposed between the anode 110 and the cathode 120.

Materials of the anode, the cathode, and one or more organic thin film layers disposed between the anode and the cathode will be explained in detail, which are for illustrative purposes and are not intended to limit the scope of the present disclosure.

The anode 110 may be formed by an electrode material having a substantially large work function. The anode 110 may be formed by metals or mixtures of, for example, copper, gold, silver, iron, chromium, nickel, manganese, palladium, platinum. The anode 110 may be formed by metal alloys, for example, copper, gold, silver, iron, chromium, nickel, manganese, palladium or platinum. The anode 110 may be formed by metal oxides or mixture of, for example, indium oxide, zinc oxide, indium tin oxide (ITO), indium zinc oxide (IZO). The anode 10 may be formed by the conductive polymers or mixtures of, for example, polyaniline, polypyrrole, poly (3-methylthiophene). In the disclosed embodiments, the anode may be formed by indium tin oxide (ITO).

The cathode 120 may be formed by an electrode material having a low work function. The cathode 120 may be formed by metals or mixtures of, for example, aluminum, magnesium, silver, indium, tin, titanium, calcium, sodium, potassium, lithium, ytterbium, lead. The cathode 120 may also be formed by multi-layer metal materials, such as LiF/Al, Liq (8-hydroxyquinoline)/Al or a mixture thereof. In the disclosed embodiments, the cathode 120 may be formed by a magnesium silver alloy or a LiF/Al double layer material.

The hole injecting layer (HIL) 160 may be formed by a material, which may facilitate the hole injection at the interface between the anode and the organic film layer and, meanwhile, may be well bonded to the surface of the ITO anode. The material forming the hole injecting layer (HIL) 160 may include, for example, copper phthalocyanine (CuPc) polyporphyrin compounds such as 4,4',4''-tri-N-naphthyl-N-anilino-triphenylamine (TNATA), poly (3,4-ethylenedioxythiophene):polystyrene sulfonate (PEDOT:PSS) having an HOMO level matching the work function of ITO, 2,3,6,7,10,11-hexacyanoyl-1,4,5,8,9,12-hexaazabenzophenanthrene (HATCN), electron-withdrawing N-heterocyclic compounds such as 2,3,6,7,10,11-hexacyanoyl-1,4,5,8,9,12-hexaazabenzophenanthrene (HATCN).

The hole transport layer (HTL) 140 and the electron blocking layer (EBL) 180 may be formed by a material having a high glass transition temperature and a high hole mobility. Materials used as the hole transport layer (HTL) 140 and the electron blocking layer (EBL) 180 may include biphenyl diamine derivatives such as diphenylnaphthylenediamine (NPD), crosslinked diamine biphenyl derivatives such as 2,2',7,7'-tetrakis (diphenylamino)-9,9'-spirobifluorene (spiro-TAD), stellate triphenylamine derivatives such as 4',4''-tris (N-carbazolyl) triphenylamine (TCTA).

The hole blocking layer (HBL) 190 and the electron transport layer (ETL) 150 may be formed by a material having a low HOMO level and high electron mobility. Materials used as the hole blocking layer and the electron transport layer may include quinoline metal complexes such as bis (8-hydroxy-2-methylquinoline)-diphenol aluminum (BAlq), tris (8-quinolinolato) aluminum (Alq), 8-hydroxyquinoline lithium, phenanthroline derivatives such as 4,7-diphenyl-1,10-phenanthroline (Bphen), imidazole derivatives such as 1,3,5,3-tris (N-phenyl-benzimidazol-2-yl) benzene (TPBI), and triazine derivatives such as 2,4,6-tricarbazolyl-1,3,5-triazine.

Figure 6:
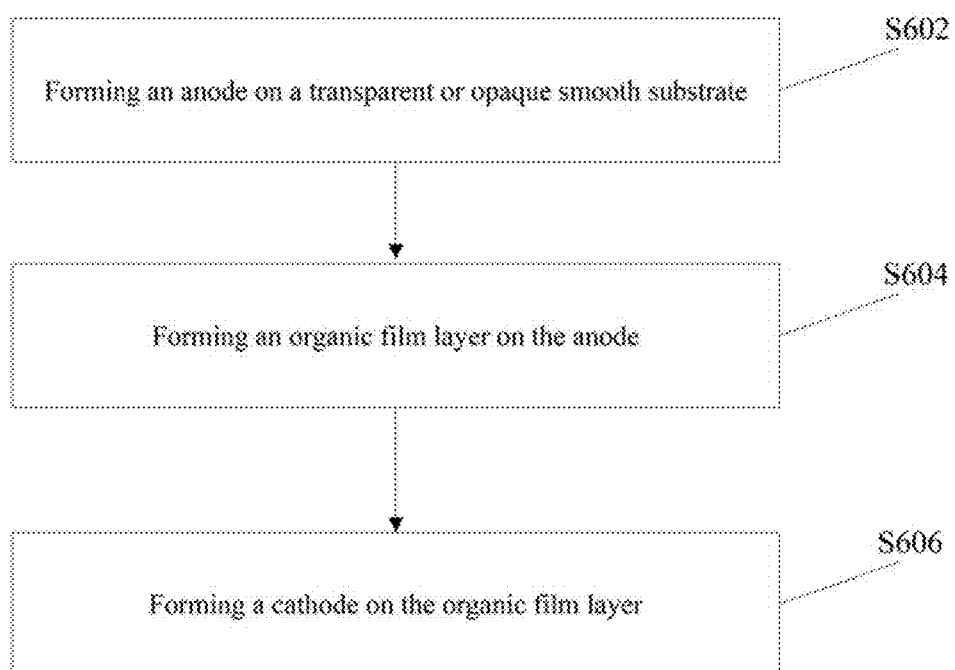
FIG. 6 illustrates a flow chart of an exemplary OLED fabrication method consistent with disclosed embodiments.

FIG. 6 illustrates a flow chart of an exemplary OLED fabrication method consistent with disclosed embodiments. As shown in FIG. 6, the OLED may be fabricated by forming an anode on a transparent or opaque smooth substrate (S602), forming an organic film layer on the anode (S604), and forming a cathode on the organic film layer (S606). The organic film layer may be formed by an existing method, such as vapor deposition, sputtering, spin coating, dipping, or ion plating.

The preparation of the certain disclosed Compounds will be explained as follows, which is for illustrative purposes and is not intended to limit the scope of the present disclosure. The disclosed compounds may be prepared in other appropriate methods.

Example 1: Preparation of Compound 1

Compound 1

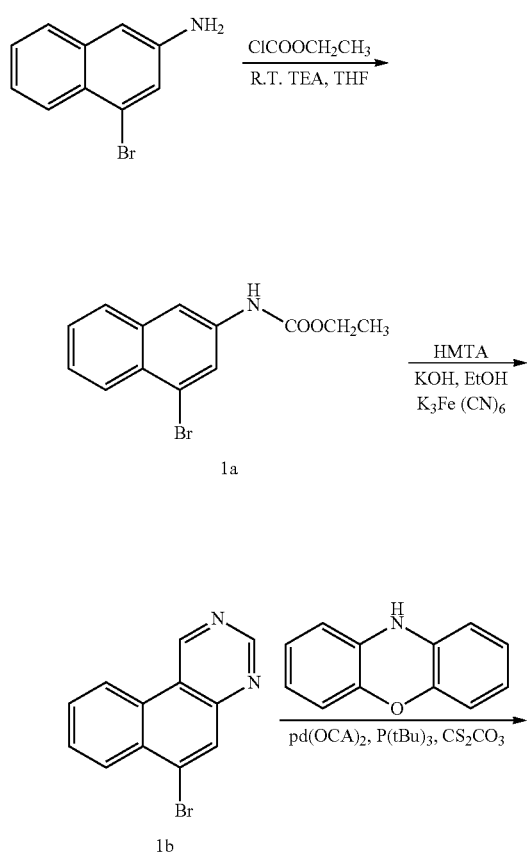

may be prepared through the following chemical reaction:

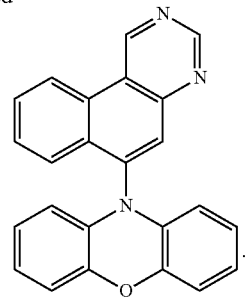

In particular, in step 1, to prepare the intermediate 1a, 3-bromo-2-naphthylamine (10 g, 45.0 mmol) and triethylamine (13.6 g, 135 mmol) were dissolved in tetrahydrofuran and stirred at room temperature. Ethyl chloroacetate (5.4 g, 49.5 mmol) was added to the reaction solution, and the mixture was stirred at room temperature for 4 hours. The solvent was evaporated under vacuum steaming, and the remaining materials were purified by silica gel column chromatography. Solid compound 1a (9.5 g, 32.4 mmol) were obtained. The yield was about 72%, and ESI-MS (m/z) obtained by the liquid phase mass spectrometer was about 293.1.

In step 2, to prepare the intermediate 1b, compound 1a (5 g, 19.3 mmol), KOH (2.1 g, 38.6 mmol), $K_3Fe(CN)_6$ (9.5 g, 28.9 mmol) and HMTA (5.2 g, 28.9 mmol) were dissolved in ethanol and refluxed for 3 hours. The ethanol was evaporated in vacuum and the solid was dissolved in ethyl acetate, stirred, filtered and washed three times with saturated brine. The solvent was evaporated under vacuum steaming, and the remaining materials were purified by silica gel column chromatography. Solid compound 1b (3.4 g, 13.1 mmol) was obtained. The yield was about 68%, and ESI-MS (m/z) obtained by the liquid phase mass spectrometer was about 258.1.

In step 3, to prepare the Compound 1, compound 1b (3.3 g, 12.6 mmol), tert-butylphosphine (0.4 g, 1.9 mmol), palladium acetate (0.4 g, 1.72 mmol) and cesium carbonate (12.3 g, 37.8 mmol) were dissolved in toluene, and heated under reflux in a nitrogen atmosphere for 10 hours. The solvent of the reaction solution was evaporated in vacuum, and the remaining material was stirred with pentane, filtered and purified by silica gel column chromatography. Solid compound 1 (2.7 g, 7.4 mmol) was obtained. The yield was about 65%, and ESI-MS (m/z) obtained by the liquid phase mass spectrometer was about 361.1.

The disclosed Compound 3 may be synthesized in a manner similar as the Compound 1, except that in the step 3, tert-butylphosphine may be replaced by 9,9-dimethylacridine.

Example 2: Preparation of Compound 5

Compound 5

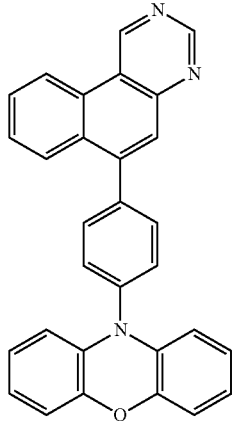 [SMILES: c1ccc2c(c1)Oc1ccccc1N2c1ccc(-c2cc3ncncc3c3ccccc23)cc1]

may be prepared through the following chemical reaction:

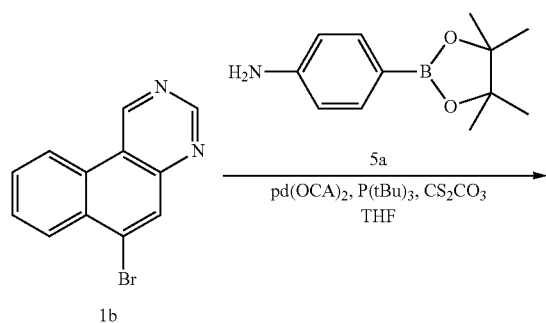

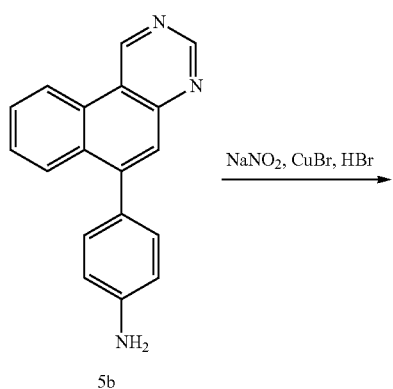

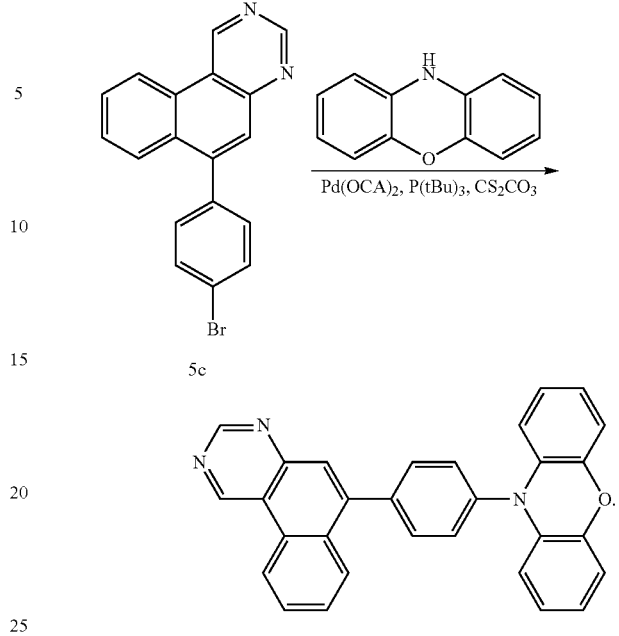

In particular, in step 1, to prepare the intermediate 5b, the compound 1b (10 g, 38.6 mmol), tert-butylphosphine (0.4 g, 5.79 mmol), palladium acetate (1.3 g, 5.79 mmol), compound 5a (10.1 g, 46.3 mmol), and cesium carbonate (12.3 g, 37.8 mmol) were dissolved in tetrahydrofuran and heated under reflux for 10 hours in a nitrogen atmosphere. After cooling, the reaction solution was extracted with toluene, washed several times with water, and dried over anhydrous magnesium sulfate. After filtering, evaporating the solvent, and purifying by silica gel column chromatography, solid compound 5b (5.4 g, 20.1 mmol) was obtained. The yield was about 52%, and ESI-MS (m/z) obtained by the liquid phase mass spectrometer was about 271.1.

In step 2, to prepare the intermediate 5c, compound 5b (5 g, 18.4 mmol) and 10 mL of 48% hydrobromic acid was mixed and stayed in ice bath, and 5 mL of aqueous sodium nitrite (3.8 g, 55.2 mmol) was added. The reaction solution was stirred for 1 hour. 5 mL of hydrobromic acid solution of cuprous bromide (2.9 g, 20.2 mmol) was added to the above mixture under ice bath, and the reaction lasted for 1 hour under ice bath, and lasted for another 2 hours after being heated 60° C. After cooling, the mixture was extracted with 50 mL of ethyl acetate. The organic layer was washed with water several times, dried over anhydrous magnesium sulfate, and filtered, and the solvent was evaporated. The remaining materials were purified by silica gel column chromatography. Solid compound 5c (4.3 g, 12.9 mmol) was obtained. The yield was about 70%, and ESI-MS (m/z) obtained by the liquid phase mass spectrometer was about 334.0.

In step 3, to prepare the Compound 5, compound 5c (3 g, 10.0 mmol), phenoxazine (2.0 g, 11 mmol), tert-butylphosphine (0.35 g, 2 mmol), palladium acetate (0.4 g, 1.8 mmol) and cesium carbonate (9.7 g, Mmol) were dissolved in toluene and heated under reflux in a nitrogen atmosphere for 10 hours. The solvent of the reaction solution was evaporated in vacuum, and the remaining material was stirred with pentane, filtered and purified by silica gel column chromatography. Solid compound 5 (2.6 g, 5.9 mmol) was obtained. The yield was about 68%, and ESI-MS (m/z) obtained by the liquid phase mass spectrometer was about 437.2.

Example 3: Preparation of Compound 25

Compound 25

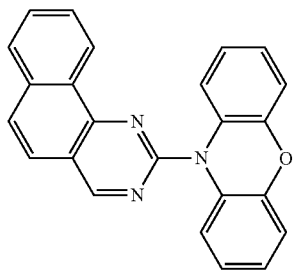 [SMILES: c1ccc2c(c1)Oc1ccccc1N2c1ncc2ccc3ccccc3c2n1]

may be prepared through the following chemical reaction:

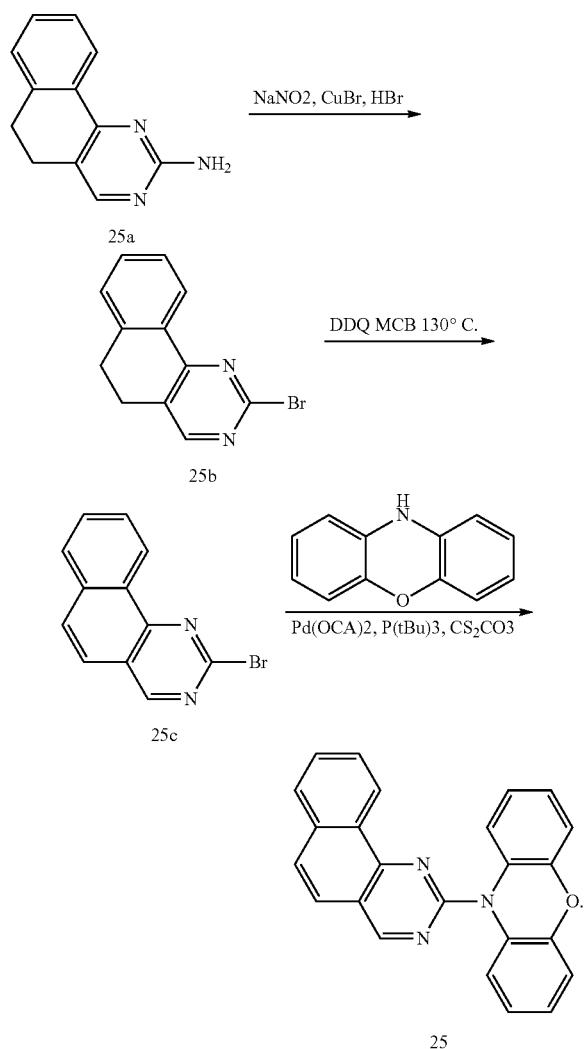

In particular, in step 1, to prepare the intermediate 25b, compound 25a (3.75 g, 19.0 mmol) and 15 mL of 48% hydrobromic acid were mixed and stayed in ice bath, and 5 mL of aqueous solution of sodium nitrite (3.8 g, 55.2 mmol) was added. The reaction solution was stirred for 1 hour. 5 mL of hydrobromic acid solution of cuprous bromide (2.9 g, 20.2 mmol) was added to the above mixture under ice bath, and the reaction lasted for 1 hour under ice bath, and lasted for another 2 hours after being heated 60° C. After cooling, the mixture was extracted with 50 mL of ethyl acetate. The organic layer was washed with water several times, dried over anhydrous magnesium sulfate, and filtered, and the solvent was evaporated. The remaining materials were purified by silica gel column chromatography. Solid compound 25b (3.4 g, 13.05 mmol) was obtained. The yield was about 690/a, and ESI-MS (m/z) obtained by the liquid phase mass spectrometer was about 260.0.

In step 2, to prepare the intermediate 25c, the compound 25b (5.2 g, 20.0 mmol) and 2,3-dichloro-5,6-dicyano-p-benzoquinone (18.2 g, 80 mmol) were dissolved in chlorobenzene and heated under reflux for 10 hours. After washing with a large amount of ethanol and sodium bicarbonate, drying over anhydrous magnesium sulfate, filtering, and evaporating the solvent, and purifying by silica gel column chromatography, solid compound 25 (4.1 g, 16 mmol) was obtained. The yield was about 80%, and ESI-MS (m/z) obtained by the liquid phase mass spectrometer was about 258.0.

In step 3, to prepare the Compound 25, the compound 25c (3.9 g, 15.0 mmol), phenoxazine (2.9 g, 16 mmol), tert-butylphosphine (0.35 g, 2 mmol), palladium acetate (0.4 g, 1.8 mmol) and cesium carbonate (9.7 g, Mmol) were dissolved in toluene and heated under reflux in a nitrogen atmosphere for 10 hours. The solvent was evaporated in vacuum and the remaining material was stirred with pentane, filtered and purified by silica gel column chromatography. Solid compound 25 (3.2 g, 8.9 mmol) was obtained. The yield was about 59%, and ESI-MS (m/z) obtained by the liquid phase mass spectrometer was about 361.1.

Example 4: Preparation of Compound 57

Compound 57

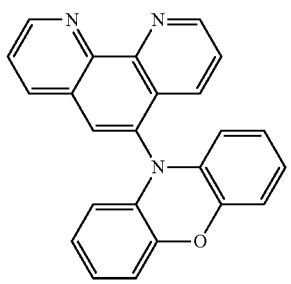 [SMILES: c1ccc2c(c1)Oc1ccccc1N2c1cc2cccnc2c2ncccc12]

may be prepared through the following chemical reaction:

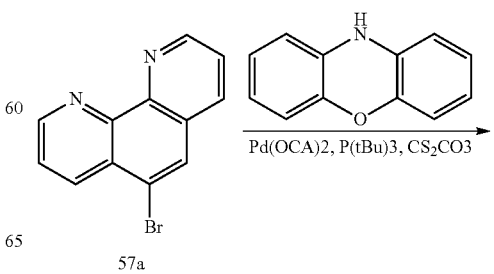

-continued

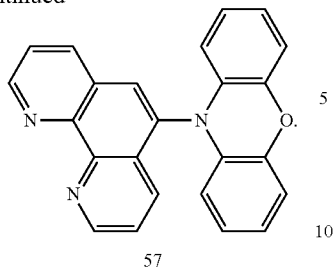

57

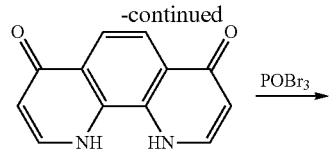

-continued

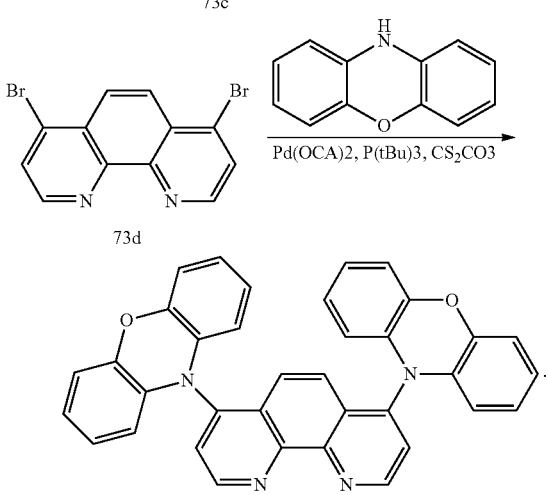

In particular, to prepare the Compound 54, the compound 57a (3.9 g, 15.0 mmol), phenoxazine (2.9 g, 16 mmol), tert-butylphosphine (0.35 g, 2 mmol), palladium acetate (0.4 g, 1.8 mmol) and cesium carbonate (9.7 g, 30 mmol) were dissolved in toluene and heated under reflux in a nitrogen atmosphere for 10 hours. The solvent was evaporated in vacuum and the remaining material was stirred with pentane, filtered and purified by silica gel column chromatography. Solid compound 57 (3.7 g, 10.2 mmol) was obtained. The yield was about 62%, and ESI-MS (m/z) obtained by the liquid phase mass spectrometer was about 361.1.

Example 5: Preparation of Compound 73

Compound 73

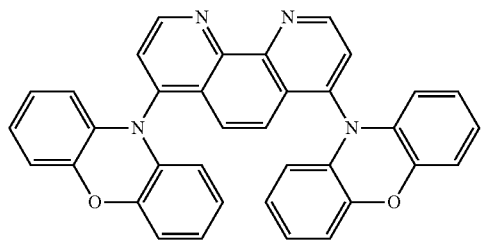 [SMILES: c1ccc2c(c1)Oc1ccccc1N2c1ccnc2c1ccc1c(N3c4ccccc4Oc4ccccc43)ccnc12]

may be prepared through the following chemical reaction:

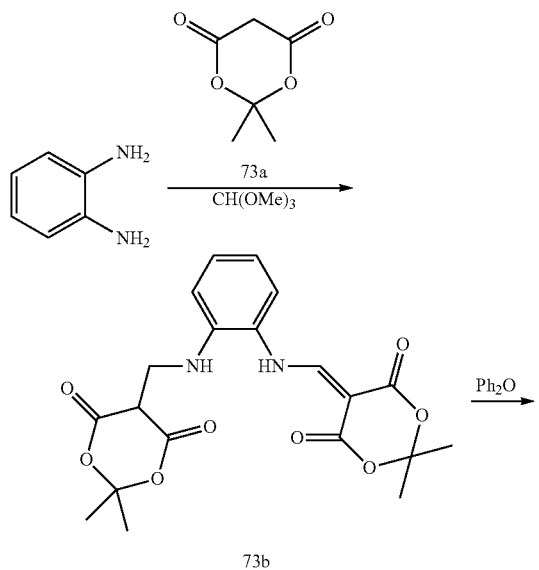

In particular, in step 1, to prepare the intermediate 73b. O-phenylenediamine (2.2 g, 20 mmol), and the compound 73a (7.2 g, 50 mmol) were dissolved in trimethoxymethane, and reacted under nitrogen atmosphere at 5° C. for 3 hours. The reaction solution was washed three times with water and saturated brine, dried over anhydrous magnesium sulfate, and the solvent was filtered and evaporated. The remaining material was purified by silica gel column chromatography. Compound 73b (5.8 g, 13.94 mmol) was obtained. The yield was about 70%, and ESI-MS (m/z) obtained by the liquid phase mass spectrometer was about 416.1.

In step 2, to prepare the intermediate 73c, the compound 73b (8.3 g, 20 mmol) was dissolved in diphenyl ether and the mixture was refluxed under nitrogen for 5 hours. The reaction solution was washed three times with water and saturated brine, dried over anhydrous magnesium sulfate and the solvent was filtered and evaporated. The remaining material was purified by silica gel column chromatography. Compound 73c (3 g, 14.3 mmol) was obtained. The yield was about 72%, and ESI-MS (m/z) obtained by the liquid phase mass spectrometer was about 212.1.

In step 2, to prepare the intermediate 73d, the compound 73c (4.2 g, 20 mmol) and tribromophosphate (14.3 g, 50 mmol) were dissolved in dry chloroform, and the mixture was refluxed for 6 hours under nitrogen. The reaction solution was washed three times with water and saturated brine, and the mixture was washed with anhydrous sulfuric acid, dried over magnesium, and the solvent was filtered and evaporated. The remaining material was purified by silica gel column chromatography. Compound 73d (4.7 g, 13.9 mmol) was obtained. The yield was about 70%, and ESI-MS (m/z) obtained by the liquid phase mass spectrometer was about 337.9.

In step 3, to prepare the Compound 73, the compound 73d (5.1 g, 15.0 mmol), phenoxazine (5.8 g, 32 mmol), t-butylphosphine (0.35 g, 2 mmol), palladium acetate (0.4 g, 1.8 mmol) and cesium carbonate (19.5 g, Mmol) were dissolved in toluene and heated under reflux in a nitrogen atmosphere for 10 hours. The solvent was evaporated in vacuum and the remaining material was stirred with pentane, filtered and purified by silica gel column chromatography. Solid Compound 73 (5.31 g, 9.8 mmol) was obtained. The yield was about 65%, and ESI-MS (m/z) obtained by the liquid phase mass spectrometer was about 542.2.

Example 6: Preparation of Compound 87

Compound 87

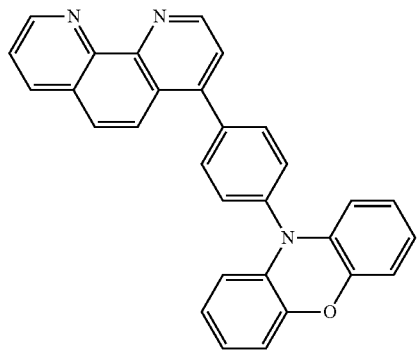 [SMILES: c1ccc2c(c1)Oc1ccccc1N2c1ccc(-c2ccnc3c2ccc2cccnc23)cc1]

may be prepared through the following chemical reaction:

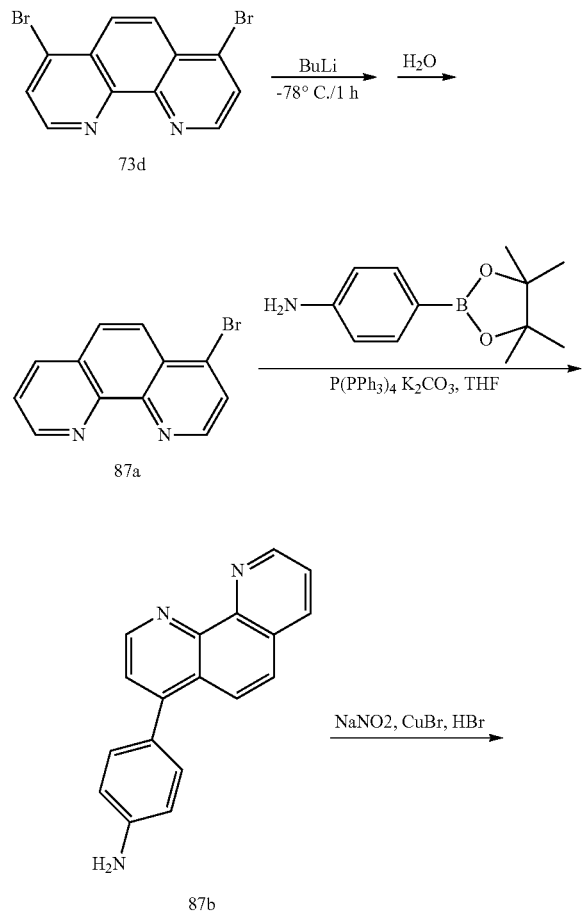

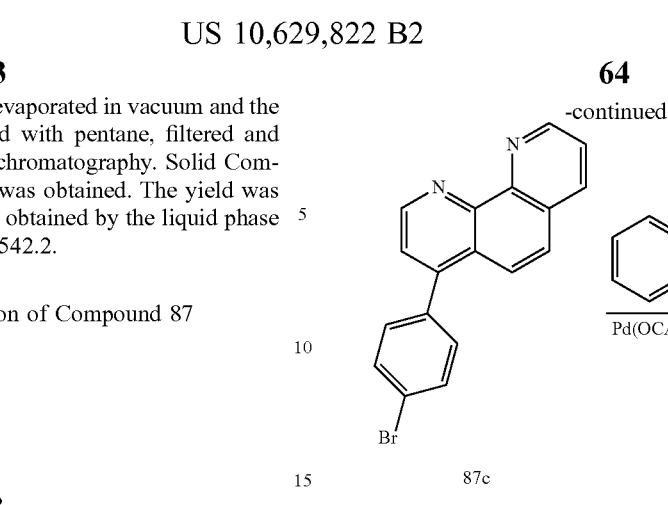

In particular, in step 1, to prepare the intermediate 87a, compound 73d (8.7 g, 16 mmol) was dissolved in 50 mL of tetrahydrofuran solution, and butyllithium (0.8 g, 14 mmol) was also added to the tetrahydrofuran solution under nitrogen and ice-salt bath, and the reactions lasted for 2 hours. After that, 20 ml of water was added to the reaction solution, and the reaction solution was washed successively with water and saturated brine, and dried. Purified by silica gel column chromatography, solid compound 87a (2.1 g, 8 mmol) was obtained. The yield was about 57%, and ESI-MS (m/z) obtained by the liquid phase mass spectrometer was about 258.0.

In step 2, to prepare the intermediate 87b, compound 87a (4.4 g, 17 mmol), tert-butylphosphine (0.4 g, 5.79 mmol), palladium acetate (1.3 g, 5.79 mmol), compound 5a (4.36 g, 20 mmol) and cesium carbonate (12.3 g, 37.8 mmol) were dissolved in tetrahydrofuran, and heated under reflux in a nitrogen atmosphere for 10 hours. After cooling, the mixture was extracted with toluene, washed several times with water, and dried over anhydrous magnesium sulfate. After filtration, the solvent was evaporated and the remaining material was purified by silica gel column chromatography. Solid compound 87b (2.7 g, 10.1 mmol) was obtained. The yield was about 59%, and ESI-MS (m/z) obtained by the liquid phase mass spectrometer was about 271.1.

In step 3, to prepare the intermediate 87c, compound 87b (5.2 g, 19.2 mmol) and 10 mL of 48% hydrobromic acid was mixed and stayed in ice bath, and 5 mL of aqueous sodium nitrite (3.8 g, 55.2 mmol) was added. The reaction solution was stirred for 1 hour. 10 mL of hydrobromic acid solution of cuprous bromide (2.9 g, 20.2 mmol) was added to the above mixture under ice bath, and the reaction lasted for 1 hour under ice bath and lasted for another 2 hours after being heated 60° C. After cooling, the mixture was extracted with 50 mL of ethyl acetate. The organic layer was washed with water several times, dried over anhydrous magnesium sulfate, and filtered, and the solvent was evaporated. The remaining materials were purified by silica gel column chromatography. Solid compound 87c (4.3 g, 12.9 mmol) was obtained. The yield was about 67%, and ESI-MS (m/z) obtained by the liquid phase mass spectrometer was about 334.0.

In step 4, to prepare the Compound 87, compound 87c (3.3 g, 10.0 mmol), phenoxazine (2.2 g, 12 mmol), tert-butylphosphine (0.35 g, 2 mmol), palladium acetate (0.4 g, 1.8 mmol) and cesium carbonate (9.7 g, 30 mmol) were dissolved in toluene, and heated under reflux under nitrogen for 10 hours. The solvent was evaporated in vacuum, and the remaining material was stirred with pentane, filtered and purified by silica gel column chromatography. Solid compound 87 (2.5 g, 5.8 mmol) was obtained. The yield was about 58%, and ESI-MS (m/z) obtained by the liquid phase mass spectrometer was about 437.2.

Example 7: Preparation of Compound 37

Compound 37

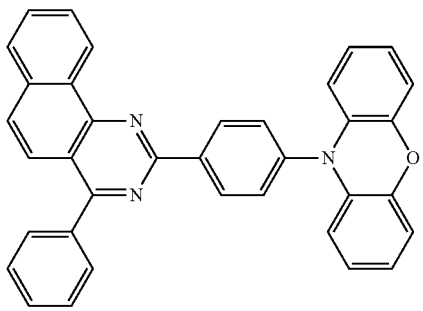 [SMILES: c1ccc(-c2nc(-c3ccc(N4c5ccccc5Oc5ccccc54)cc3)nc3c2ccc2ccccc23)cc1]

may be prepared through the following chemical reaction:

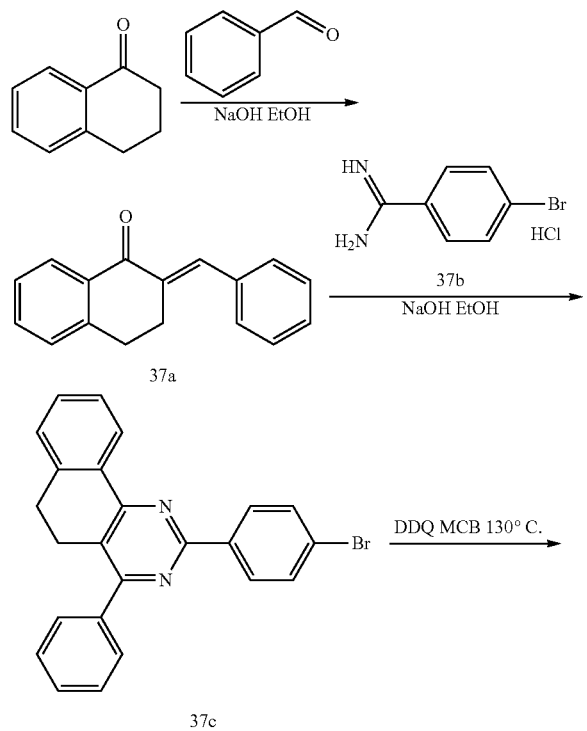

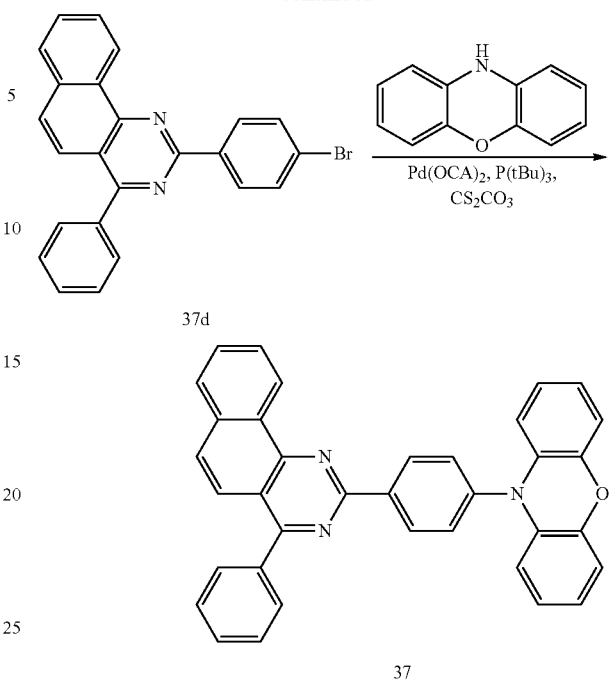

In particular, in step 1, to prepare the intermediate 37a, 1-tetralone (2.9 g, 20.0 mmol), benzaldehyde (2.65 g, 25 mmol), and sodium hydroxide (1.8 g, 45 mmol) were dissolved in ethanol and heated under reflux for 5 hours. The solvent was dried in vacuum and the solid was dissolved in ethyl acetate. The mixture was stirred, filtered, washed with water and saturated brine, and dried over anhydrous magnesium sulfate. The solvent was evaporated under a vacuum steaming vessel and the remaining material was purified by silica gel column chromatography. Solid compound 37a (3.5 g, 15 mmol) was obtained. The yield was about 75%, and ESI-MS (m/z) obtained by the liquid phase mass spectrometer was about 234.1.

In step 2, to prepare the intermediate 37c, the compound 37a (4.7 g, 20.0 mmol), 37b (4.9 g, 24.7 mmol) and sodium hydroxide (1.4 g, 35 mmol) were dissolved in ethanol and heated under reflux for 3 hours. The mixture was stirred for 3 hours and the solvent was dried in vacuum. The solid was then dissolved in ethyl acetate, stirred, filtered, washed three times with water and saturated brine, dried over anhydrous magnesium sulfate, and purified by silica gel column chromatography. Solid compound 37c (5.0 g, 12 mmol) was obtained. The yield was about 68%, and ESI-MS (m/z) obtained by the liquid phase mass spectrometer was about 414.1.

In step 3, to prepare the Compound 37, the compound 37c (8.3 g, 20.0 mmol) and 2,3-dichloro-5,6-dicyano-p-benzoquinone (18.2 g, 80 mmol) were dissolved in chlorobenzene and heated under reflux for 10 hours. The mixture was washed with a large amount of ethanol and sodium bicarbonate, dried over anhydrous magnesium sulfate, and the solvent was filtered and evaporated. The remaining material was purified by silica gel column chromatography. Solid compound 37d (6.2 g, 15 mmol) was obtained. The yield was about 75%, and ESI-MS (m/z) obtained by the liquid phase mass spectrometer was about 412.0.

Example 8: Preparation of Compound 155

Compound 155

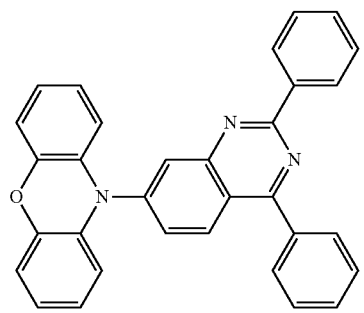 [SMILES: c1ccc(-c2nc(-c3ccccc3)c3ccc(N4c5ccccc5Oc5ccccc54)cc3n2)cc1]

may be prepared through the following chemical reaction:

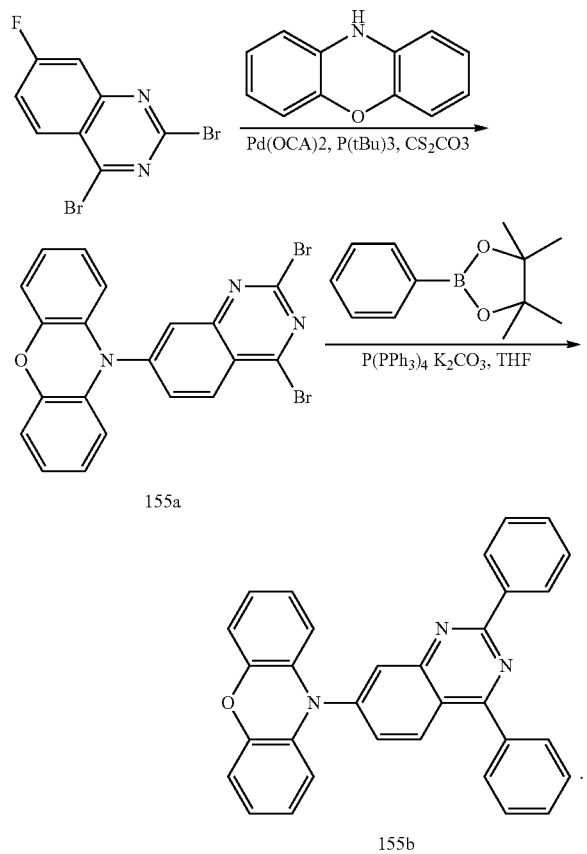

In particular, in step 1, to prepare the intermediate 155a, 2,4-dibromo-7,-fluoro-quinazoline (3.1 g, 10.1 mmol), phenoxazine (2.2 g, 12 mmol), tert-butylphosphine (0.35 g, 2 mmol), palladium acetate (0.4 g, 1.8 mmol) and cesium carbonate (9.7 g, 30 mmol) were dissolved in toluene, and heated under reflux in a nitrogen atmosphere for 10 hours. The solvent was evaporated in vacuum and the remaining material was stirred with pentane, filtered and purified by silica gel column chromatography. Solid compound 155a (2.7 g, 5.7 mmol) was obtained. The yield was about 56%, and ESI-MS (m/z) obtained by the liquid phase mass spectrometer was about 468.9.

In step 2, to prepare the Compound 155, compound 155a (8.0 g, 17 mmol), t-butylphosphine (0.4 g, 5.79 mmol), palladium acetate (1.3 g, 5.79 mmol), phenylboronic acid (4.1 g, 20 mmol) and cesium carbonate (12.3 g, 37.8 mmol) were dissolved in tetrahydrofuran and heated under reflux in a nitrogen atmosphere for 10 hours. After cooling, the mixture was extracted with toluene, washed several times with water, and dried over anhydrous magnesium sulfate. The remaining material was filtered and purified by silica gel column chromatography. Solid Compound 155 (4.5 g, 9.8 mmol) was obtained. The yield was about 58%, and ESI-MS (m/z) obtained by the liquid phase mass spectrometer was about 463.2.

The disclosed Compound 157 may be synthesized in a manner similar as the Compound 155, except that, in the step 1, phenoxazine may be replaced by 9,9-dimethylacridine.

The other disclosed compounds may be synthesized in a similar manner, which is not repeated here.

Example 9: Simulation of Compounds

The energy difference between single and triplet states of the disclosed compounds may be obtained by Guassian 09 software (Guassian Inc.). The energy difference ΔEst may be simulated according to the simulation method described in J. Chem. Theory Comput., 2013 (DOI: 10.1021/ct400415r). The molecular structure optimization and molecular excitation may be performed by using the TD-DFT method "B3LYP" and the base group "6-31g (d)". For illustrative purposes, a simulation is performed for the Compounds 3, 5, 37, 73, 78, 119, and 157 selected from the Compounds 1-198. The simulation results of the Compounds 5, 37, 73, 78, 119, and 157 are shown in Table 1.

TABLE 1

| Simulation results of seven exemplary compounds | | | |
|---|---|---|---|
| Compound | $S_1$ (eV) | $T_1$ (eV) | $\Delta E_{st}$ (eV) |
| 3 | 2.6760 | 2.6449 | 0.0311 |
| 5 | 2.8277 | 2.6323 | 0.1954 |
| 37 | 2.5768 | 2.4611 | 0.1157 |
| 73 | 2.5995 | 2.5865 | 0.013 |
| 78 | 2.9389 | 2.6495 | 0.2894 |
| 119 | 2.5333 | 2.4881 | 0.0452 |
| 157 | 2.7750 | 2.4944 | 0.2806 |

As shown in Table 1, the energy difference between single and triplet states of disclosed compounds are substantially small, which may enable efficient reverse intersystem crossing (RISC) in the compounds and provide TADF properties. Thus, the disclosed compounds may have a heat activated delayed fluorescence (TADF) material luminescence mechanism, which may be used as a new type of TADF material in the organic optoelectronic devices to improve the luminous efficiency. Moreover, the disclosed compounds may be prepared without expensive metal complexes, thereby reducing the manufacturing cost and widening the applications.

Example 10: Organic Optoelectronic Device Fabrication and Testing

Figure 7:
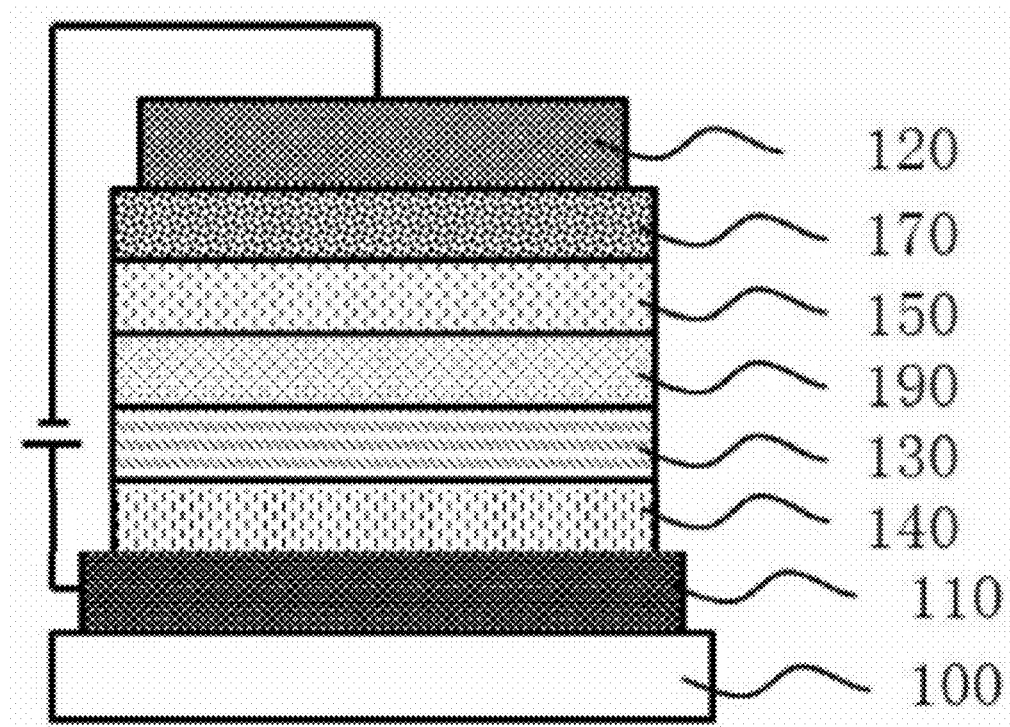
FIG. 7 illustrates a schematic diagram of another exemplary OLED consistent with disclosed embodiments.

To evaluate the performance of the disclosed organic optoelectronic devices, six exemplary organic optoelectronic devices (named as 1st disclosed organic optoelectronic device to the 7th disclosed organic optoelectronic device), and two reference organic optoelectronic devices (named as 1st reference organic optoelectronic device and the 2nd reference organic optoelectronic device) were fabricated. The 1st to the 7th disclosed organic optoelectronic devices and the 1st to the 2nd reference organic optoelectronic devices have the same structure shown in FIG. 7, except that the materials for forming various layers are different.

To fabricate the 1st disclosed organic optoelectronic device, a substrate coated with a 100-nm-thick ITO film as the anode 110 was ultrasonically cleaned with distilled water, acetone, isopropanol, then dried in an oven, treated with UV for 30 minutes, and transferred to a vacuum evaporation chamber. Various organic films were vapor-deposited under a vacuum of 2×10-6 Pa. 60-nm-thick diphenylnaphthalenediamine (NPD) film and 10-nm-thick 4,4',4''-tris (N-carbazolyl) triphenylamine (TCTA) film were vapor-deposited on the anode 110 to form a hole transport layer (HTL) 140. 6 wt % Ir (ppy)$_3$ was used as the green phosphorescent dopant material and 94 wt % Compound 3 was used as the host material, which were vapor-deposited on the hole transport layer (HTL) 140 to form a 30-nm-thick light-emitting layer 130.

Then, bis (8-hydroxy-2-methylquinoline)-diphenol aluminum (BAlq) was vapor-deposited on the light-emitting layer 130 to form a 5-nm-thick hole blocking layer (HBL) 190. 4,7-diphenyl-1,10-phenanthroline (Bphen) was vapor-deposited on the hole blocking layer (HBL) 190 to form a 20-nm-thick electron transport layer (ETL) 150. 1-nm-thick LiF and 100-nm-thick Al were successively deposited as an electron injection layer (EIL) 170 and the cathode 120 on the electron transport layer (ETL) 150, respectively. The fabricated 1st disclosed organic optoelectronic device has a structure of ITO (100 nm)/NPD (60 nm)/TCTA (10 nm)/Ir (ppy)$_3$: Compound 3 (6 wt %:94 wt %, 30 nm)/BAlq (5 nm)/Bphen (20 nm)/LiF (1 nm)/Al (100 nm).

The 2nd disclosed organic optoelectronic device was fabricated in the same manner as 1st disclosed organic optoelectronic device, except that Compound 37 was adopted instead of Compound 3 as the host material in the 2nd disclosed organic optoelectronic device.

The 3rd disclosed organic optoelectronic device was fabricated in the same manner as 1st disclosed organic optoelectronic device, except that Compound 73 was adopted instead of Compound 3 as the host material in the 3rd disclosed organic optoelectronic device.

The 4th disclosed organic optoelectronic device was fabricated in the same manner as 1st disclosed organic optoelectronic device, except that Compound 119 was adopted instead of Compound 3 as the host material in the 3rd disclosed organic optoelectronic device.

The 1st reference organic optoelectronic device was fabricated in the same manner as 1st disclosed organic optoelectronic device, except that 6 wt % Ir (ppy)$_3$ was adopted as the dopant material, and 94 wt % CBP was adopted as the host material, which were vapor-deposited on the hole transport layer (HTL) 140 to form a 30-nm-thick light-emitting layer 130.

The 5th disclosed organic optoelectronic device was fabricated in the same manner as 1st disclosed organic optoelectronic device, except that 5 wt % Compound 5 was adopted as the dopant material, and 95 wt % DPEPO was adopted as the host material, which were vapor-deposited on the hole transport layer (HTL) 140 to form a 30-nm-thick light-emitting layer 130.

The fabricated 4th disclosed organic optoelectronic device has a structure of ITO (100 nm)/NPD (60 nm)/TCTA (10 nm)/Compound 5: DPEPO (5 wt %:95 wt %, 30 nm)/BAlq (5 nm)/Bphen (20 nm)/LiF (1 nm)/Al (100 nm).

The 6th disclosed organic optoelectronic device was fabricated in the same manner as 5th disclosed organic optoelectronic device, except that Compound 78 was adopted instead of Compound 5 as the dopant material in the 5th disclosed organic optoelectronic device.

The 7th disclosed organic optoelectronic device was fabricated in the same manner as 5th disclosed organic optoelectronic device, except that Compound 157 was adopted instead of Compound 5 as the dopant material in the 5th disclosed organic optoelectronic device.

The 2nd reference organic optoelectronic device was fabricated in the same manner as 5th disclosed organic optoelectronic device, except that 5 wt % DPAVB was adopted as the dopant material, and 95 wt % DPEPO was adopted as the host material, which were vapor-deposited on the hole transport layer (HTL) 140 to form a 30-nm-thick light-emitting layer 130.

The chemical formulas of DPAVB, DPEPO, Ir(ppy)$_3$, BAlq, Bphen, a-NPD, TCTA, and CBP are shown below.

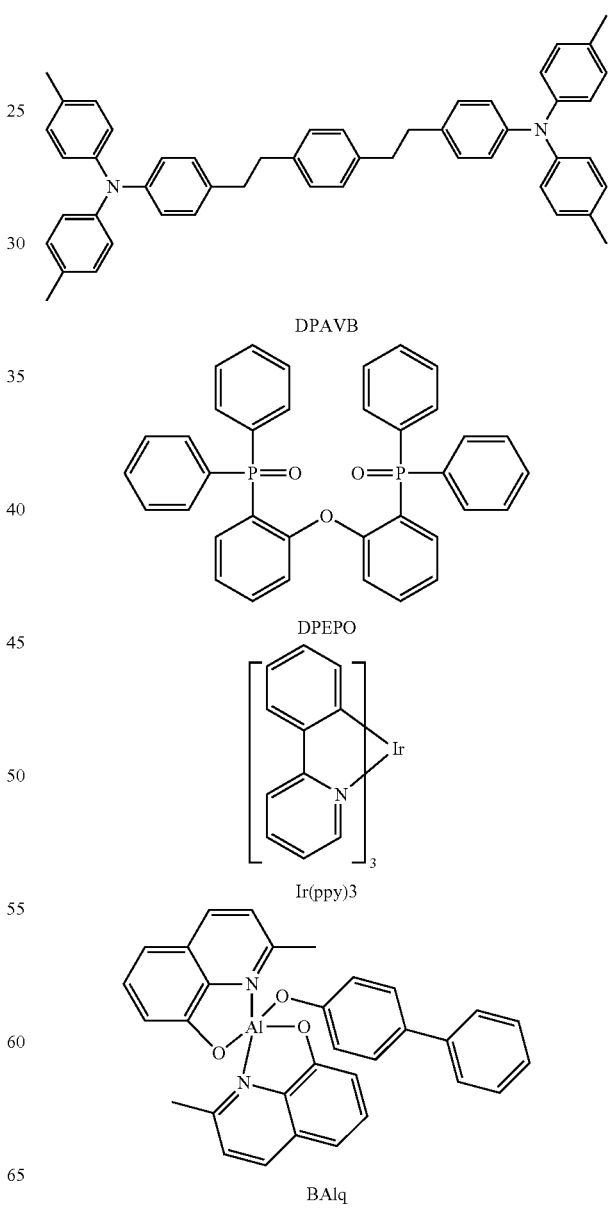

-continued

Bphen

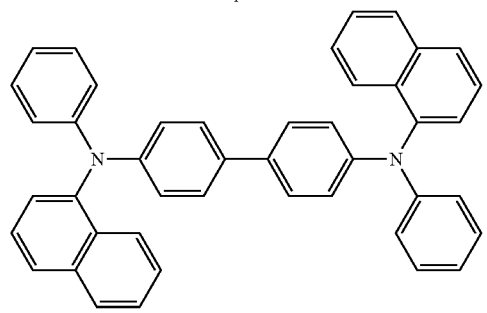
a-NPD

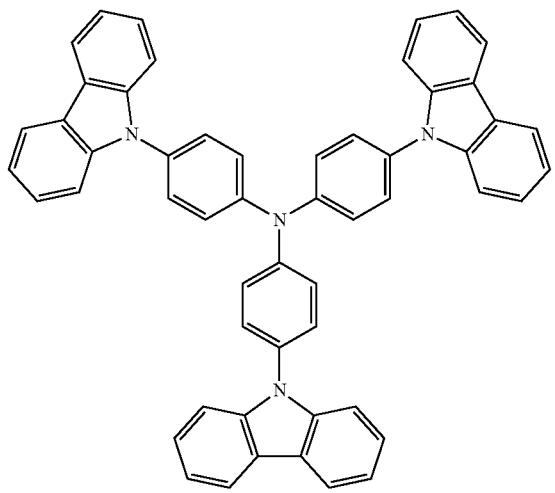
TCTA

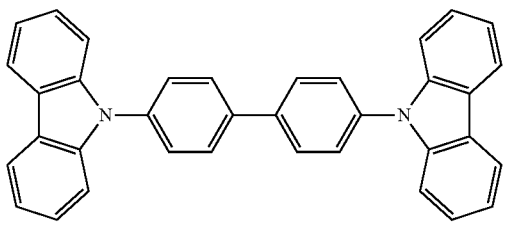
CBP

The current of the 1st to 7th disclosed organic optoelectronic devices and the 1st to 2nd reference organic optoelectronic devices under different voltages was measured by Keithley 2365A digital nanovolt meter, respectively. Then the corresponding current density was calculated by dividing the current by the light-emitting area. The luminance and radiant energy density of the 1st to 7th disclosed organic optoelectronic devices and the 1st to 2nd reference organic optoelectronic devices under different voltages was measured by Konicaminolta CS-2000 spectrophotometer, respectively. Based on the current density and the luminance under different voltages, the current efficiency (Cd/A) and the external quantum efficiency (EQE) under a given current density (10 mA/cm2) was obtained.

The testing results of the 1st to 4th disclosed organic optoelectronic devices in which the disclosed compounds are used as the host material and the 1st reference organic optoelectronic device are shown in the following Table 2.

TABLE 2

Testing results of the 1st to 4th disclosed organic optoelectronic devices and the 1st reference organic optoelectronic device

| | Voltage (V) | Current efficiency (Cd/A) | EQE (%) | Color |
|---|---|---|---|---|
| 1st disclosed organic optoelectronic device | 4.5 | 44.2 | 18.1 | Green |
| 2nd disclosed organic optoelectronic device | 4.7 | 44.0 | 17.6 | Green |
| 3rd disclosed organic optoelectronic device | 4.6 | 42.6 | 16.8 | Green |
| 4th disclosed organic optoelectronic device | 4.6 | 43.7 | 17.4 | Green |
| 1st reference organic optoelectronic device | 5.1 | 40.3 | 15.6 | Green |

The testing results of the 5th to 7th disclosed organic optoelectronic devices in which the disclosed compounds are used as the guest dopant material and the 2nd reference organic optoelectronic device are shown in the following Table 3.

TABLE 3

Testing results of the 5th to 7th disclosed organic optoelectronic devices and the 2nd reference organic optoelectronic device

| | Voltage (V) | Current efficiency (Cd/A) | EQE (%) | Color |
|---|---|---|---|---|
| 5th disclosed organic optoelectronic device | 7.3 | 8.8 | 7.6 | Blue |
| 6th disclosed organic optoelectronic device | 7.7 | 7.9 | 6.8 | Blue |
| 7th disclosed organic optoelectronic device | 7.5 | 8.3 | 7.1 | Blue |
| 2nd reference organic optoelectronic device | 8.8 | 5.5 | 4.9 | Blue |

According to the testing results shown in Table 2, under the same current density (10 mA/cm2), the 1st to 4th disclosed organic optoelectronic devices have a driving voltage lower than 5V, current efficiency higher than 40 Cd/A, and external quantum efficiency (EQE) larger than 15. That is, the disclosed compounds may enable the 1st to 4th disclosed organic optoelectronic devices to have a lower driving voltage, higher current efficiency and external quantum efficiency (EQE). The testing results shown in Table 2 may indicate that the disclosed compounds may be used as host materials.

According to the testing results shown in Table 3, under the same current density (10 mA/cm$^2$), the 5th to 7th disclosed organic optoelectronic devices have a lower driving voltage, higher current efficiency and external quantum efficiency (EQE) than the 2nd reference organic optoelectronic device. The testing results shown in Table 3 may indicate that the disclosed compounds may be used as dopant materials or co-doping materials. According to the testing results shown in Table 2 and Table 3, the optoelectronic device comprising the disclosed compounds may have excellent luminescent properties.

The other disclosed compounds may also enable the corresponding organic optoelectronic devices to have a lower driving voltage, higher current efficiency and external quantum efficiency (EQE), i.e., excellent luminescent properties.

The description of the disclosed embodiments is provided to illustrate the present invention to those skilled in the art. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A compound of the following chemical formula (I):

chemical formula (I), wherein in the chemical formula (I):

n denotes a positive integer and $1 \leq n \leq 5$;

a chemical group B has the following chemical formula (II):

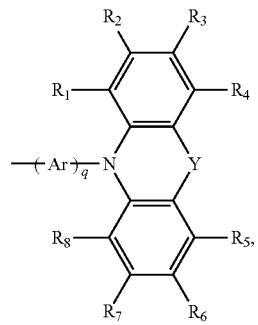

chemical formula (II), wherein each chemical group B has a same or different structure when n>1, and in the chemical formula (II):
$R_1$ to $R_8$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, Y is selected from O, S, substituted or unsubstituted imino, and substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, Ar is selected from $C_6$ to $C_{30}$ aryl, and $C_2$ to $C_{30}$ heteroaryl, and q is an integer and $1 \leq q \leq 3$; and a chemical group A has the following chemical formula (IV):

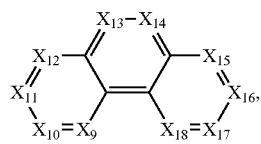

chemical formula (IV), wherein in the chemical formula (IV):
$X_{15}$ and $X_{17}$ are selected from N while $X_9$ to $X_{14}$, $X_{16}$ and $X_{18}$ are selected from C, or $X_{10}$ and $X_{12}$ are selected from N while $X_9$, $X_{11}$ and $X_{13}$ to $X_{18}$ are selected from C, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and the chemical group B is connected to C.

2. The compound according to claim 1, wherein:

the chemical formula (IV) is

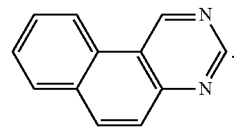

3. The compound according to claim 1, wherein:

the $C_6$ to $C_{30}$ aryl is selected from phenyl and naphthyl.

4. The compound according to claim 1, wherein:

$R_1$ to $R_8$ are selected from hydrogen, and Y is selected from O, S, and dimethyl substituted Si(—Si(CH$_3$)$_2$—).

5. The compound according to claim 1, wherein:

q represents an integer of 1.

6. The compound according to claim 1, comprising a compound selected from the following:

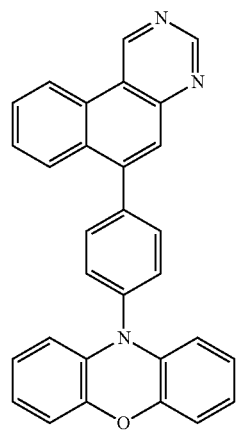 [SMILES: c1ccc2c(c1)Oc1ccccc1N2c1ccc(-c2cc3ncncc3c3ccccc23)cc1]

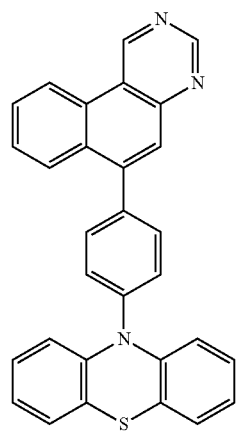

75
-continued
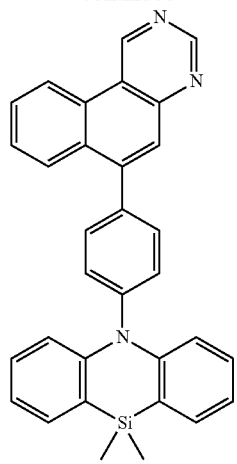
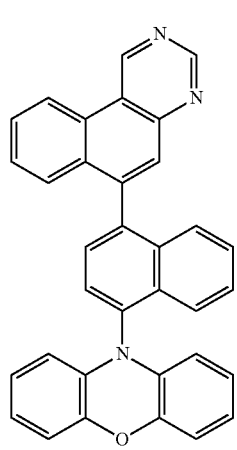
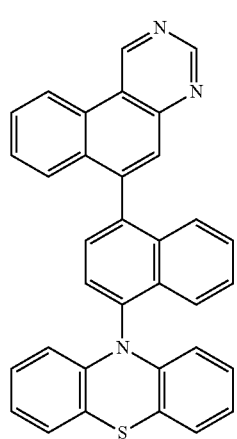
76
-continued
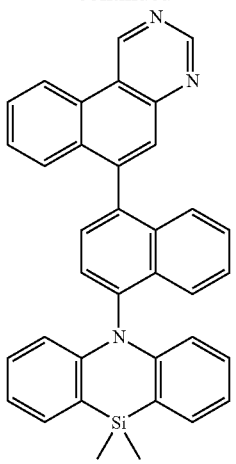
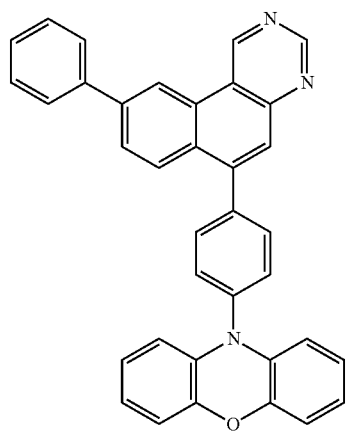
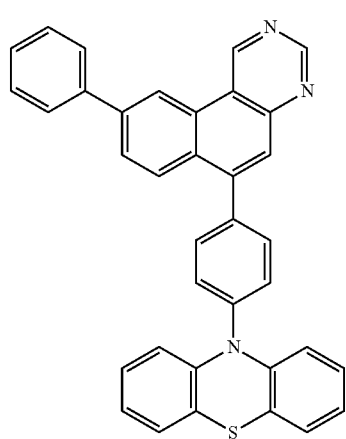

-continued

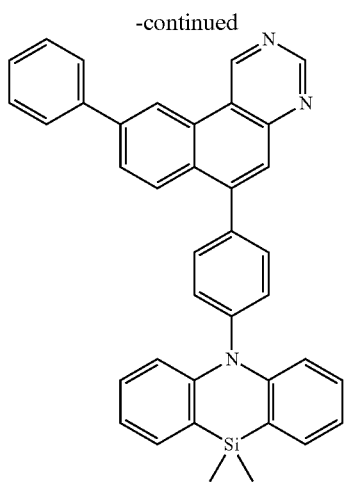

7. The compound according to claim 1, wherein:
an energy difference between a lowest singlet excited state $S_1$ and a lowest triplet excited state $T_1$ of the compound is configured to be ΔEst, wherein ΔEst≤0.30 eV.

8. An organic optoelectronic device, comprising:
an anode;
a cathode; and
one or more organic thin film layers disposed between the anode and the cathode,
wherein at least one of the one or more organic thin film layers includes one or more compounds each having the following chemical formula (I):

A─[B]$_n$  chemical formula (I), wherein in the chemical formula (I):
n denotes a positive integer and 1≤n≤5;
a chemical group B has the following chemical formula (II):

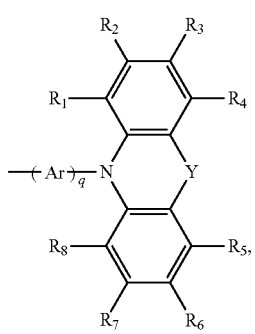

chemical formula (II),
wherein each chemical group B has a same or different structure when n>1, and in the chemical formula (II):
$R_1$ to $R_8$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
Y is selected from O, S, substituted or unsubstituted imino, and substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, Ar is selected from $C_6$ to $C_{30}$ aryl, and $C_2$ to $C_{30}$ heteroaryl, and
q is an integer and 1≤q≤3; and
a chemical group A has the following chemical formula (IV):

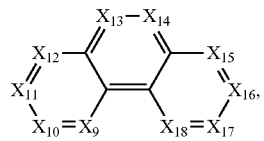

chemical formula (IV),
wherein in the chemical formula (IV):
$X_{15}$ and $X_{17}$ are selected from N while $X_9$ to $X_{14}$, $X_{16}$ and $X_{18}$ are selected from C, or $X_{10}$ and $X_{12}$ are selected from N while $X_9$, $X_{11}$ and $X_{13}$ to $X_{18}$ are selected from C, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and
the chemical group B is connected to C.

9. The organic optoelectronic device according to claim 8, wherein:
the one or more compounds are heat activated delayed fluorescence (TADF) materials.

10. The organic optoelectronic device according to claim 8, wherein:
the at least one of the one or more organic thin film layers disposed between the anode and the cathode is a light-emitting layer, wherein the light-emitting layer includes the one or more compounds.

11. The organic optoelectronic device according to claim 10, wherein:
the one or more compounds are used as a dopant material, a co-doping material, or a host material in the light-emitting layer.

12. The organic optoelectronic device according to claim 8, wherein:
the one or more organic thin film layers further include at least one of a hole transport layer, a hole injection layer, an electron blocking layer, a hole blocking layer, an electron transport layer, and an electron injection layer.

13. The organic optoelectronic device according to claim 12, wherein:
at least one of the hole transport layer, the hole injection layer, the electron blocking layer, the hole blocking layer, the electron transport layer, and the electron injection layer includes the one or more compounds.

14. The organic optoelectronic device according to claim 10, wherein:
the one or more organic thin film layers further include a hole transport layer disposed between the light-emitting layer and the anode.

15. The organic optoelectronic device according to claim 10, wherein:
the one or more organic thin film layers further include a hole transport layer and an electron transport layer,
wherein the hole transport layer is disposed between the light-emitting layer and the anode, and
the electron transport layer is disposed between the light-emitting layer and the cathode.

16. The organic optoelectronic device according to claim 10, wherein:
the one or more organic thin film layers further include a hole transport layer, an electron transport layer, an electron injection layer and a hole injection layer,
wherein the hole transport layer and the hole injection layer are disposed between the light-emitting layer and the anode, and
the electron transport layer and the electron injection layer are disposed between the light-emitting layer and the cathode.

17. The compound according to claim 1, wherein n=2 and Y in each of two chemical groups B is different from each other.

18. A compound of the following chemical formula (I):

A─[B]$_n$   chemical formula (I), wherein in the chemical formula (I):
n denotes a positive integer and 1≤n≤5;
a chemical group B has the following chemical formula (II):

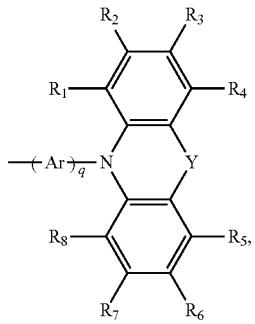

chemical formula (II),
wherein each chemical group B has a same or different structure when n>1, and in the chemical formula (II):
$R_1$ to $R_8$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
Y is substituted or unsubstituted silylene, wherein a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
Ar is selected from $C_6$ to $C_{30}$ aryl, and $C_2$ to $C_{30}$ heteroaryl, and
q is an integer and 1≤q≤3; and
a chemical group A has one of following chemical formula (III) and (IV):

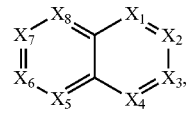

chemical formula (III), and

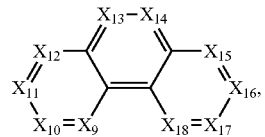

chemical formula (IV),
wherein in the chemical formula (III):
$X_1$ to $X_8$ are independently selected from C and N, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and
the chemical group B is connected to C,
wherein in the chemical formula (IV):
$X_{15}$ and $X_{17}$ are selected from N while $X_9$ to $X_{14}$, $X_{16}$ and $X_{18}$ are selected from C, or $X_{10}$ and $X_{12}$ are selected from N while $X_9$, $X_{11}$ and $X_{13}$ to $X_{18}$ are selected from C, when N is selected, a substituent is not included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included, and
the chemical group B is connected to C.

* * * * *